(12) United States Patent
Umezawa et al.

(10) Patent No.: US 8,124,424 B2
(45) Date of Patent: Feb. 28, 2012

(54) SINGLE MOLECULE-FORMAT BIOLUMINESCENT PROBE

(75) Inventors: Yoshio Umezawa, Tokyo (JP);
Moritoshi Sato, Tokyo (JP); Hiroaki Tao, Ibaraki (JP); SungBae Kim, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 12/448,881

(22) PCT Filed: Jan. 15, 2008

(86) PCT No.: PCT/JP2008/050370
§ 371 (c)(1),
(2), (4) Date: Sep. 2, 2009

(87) PCT Pub. No.: WO2008/084869
PCT Pub. Date: Jul. 17, 2008

(65) Prior Publication Data
US 2010/0273150 A1  Oct. 28, 2010

(30) Foreign Application Priority Data

Jan. 12, 2007  (JP) .................. 2007-005144

(51) Int. Cl.
G01N 33/566 (2006.01)
G01N 33/53 (2006.01)
G01N 33/567 (2006.01)
C12Q 1/66 (2006.01)
C07K 1/00 (2006.01)
C12N 15/00 (2006.01)
C12N 5/00 (2006.01)

(52) U.S. Cl. ............ 436/501; 435/7.8; 435/8; 435/7.21; 435/320.1; 435/325; 530/350; 530/402

(58) Field of Classification Search ........................ None
See application file for complete search history.

(56) References Cited

U.S. PATENT DOCUMENTS
2007/0275428 A1 * 11/2007 Gambhir et al. .................. 435/8
2009/0113563 A1 * 4/2009 Umezawa et al. .............. 800/14

FOREIGN PATENT DOCUMENTS
CA  2601952  * 8/2005

OTHER PUBLICATIONS

Kim et al (a). 2007. Anal Chem. 79:17874-1880.*
Kim et al (b). 2007. Anal Chem. 79:4820-4826.*
Promega Technical Manual, www.promega.com, revised Aug. 2006, downloaded, Jan. 6, 2011.*
Eck et al., 1996 Goodman & Gilman's The Pharmacological Basis of Therapeutics, McGraw-Hill, New York, p. 77-101.*
Ozawa et al. 2001. Anal Chem 73:2516-2521.*
Conti et al. 1996. Structure 4:287-298.*
Paulmurugan, Paul, et al., "An intramolecular folding sensor for imaging receptor-ligand interactions", PNAS, Oct. 24, 2006, 103 (43): 15883-15888.

* cited by examiner

*Primary Examiner* — Shulamith H Shafer
(74) *Attorney, Agent, or Firm* — Wenderoth, Lind & Ponack, L.L.P.

(57) ABSTRACT

The claimed invention comprises a single molecule-format bioluminescent probe for detecting a target-specific ligand in a living cell, which comprises, a ligand-binding molecule of which conformation is changed upon binding to the ligand, wherein the ligand-binding molecule comprises a ligand-binding domain (LBD) of a nuclear receptor and an LBD-interacting domain that is a co-activator peptide of said nuclear receptor, and an N-terminal polypeptide and a C-terminal polypeptide of a click beetle luciferase (N-CBLuc and C-CBLuc), which flank each end of the ligand-binding molecule, respectively, wherein the N-CBLuc and the C-CBLuc self-complement to generate a luminescent signal only upon binding of the ligand to the ligand-binding molecule.

8 Claims, 22 Drawing Sheets

Fig. 10
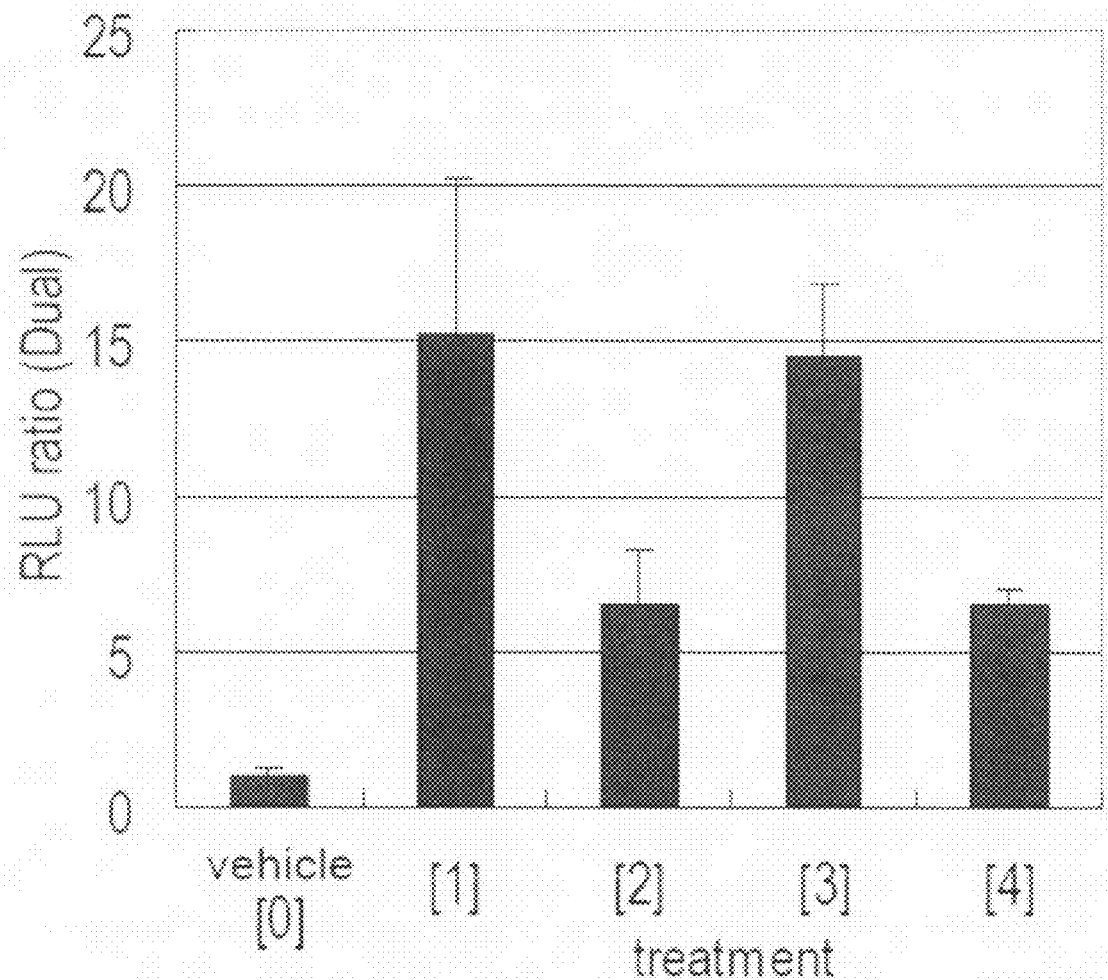
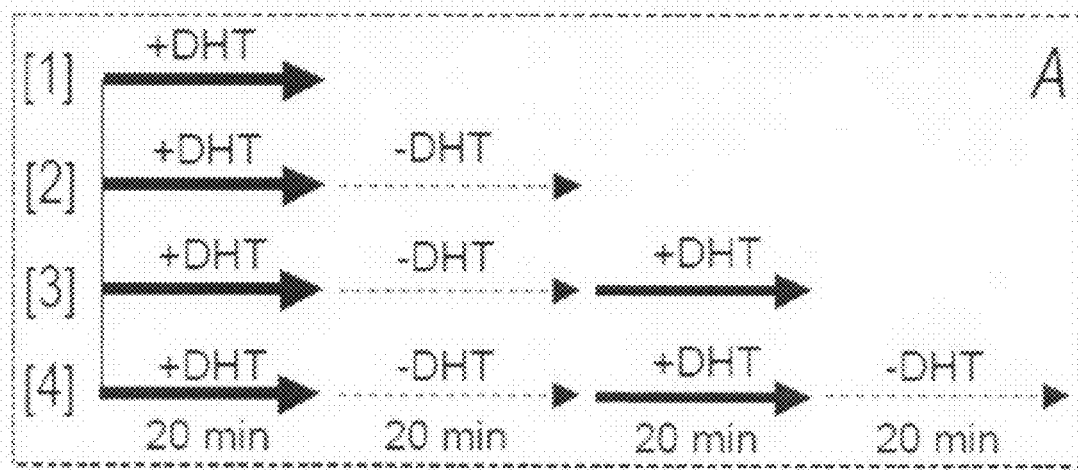

Fig. 12 a

```
           10         20         30         40         50         60
     MVKREKNVIY GPEPLHPLED LTAGEMLFRA LRKHSHLPQA LVDVVGDESL SYKEFFEATV 70         80         90        100        110        120
     LLAQSLHNCG YKMNDVVSIC AENNTRFFIP VIAAWYIGMI VAPVNESYIP DELCKVMGIS 130        140        150        160        170        180
     KPQIVFTTKN ILNKVLEVQS RTNFIKRIII LDTVENIHGC ESLPNFISRY SDGNIANFKP 190        200        210        220        230        240
     LHFDPVEQVA AILCSSGTTG LPKGVMQTHQ NICVRLIHAL DPRYGTQLIP GVTVLVYLPF 250        260        270        280        290        300
     FHAFGFHITL GYFMVGLRVI MFRRFDQEAF LKAIQDYEVR SVINVPSVIL FLSKSPLVDK 310        320        330        340        350        360
     YDLSSLRELC CGAAPLAKEV AEVAAKRLNL PGIRCGFGLT ESTSAIIQTL GDEFKSGSLG 370        380        390        400        410        420
     RVTPLMAAKI ADRETGKALG PNQVGELCIK GPMVSKGYVN NVEATKEAID DQGWLHSGDF
                                   ▲                              ▲
          430        440        450        460        470        480
     GYYDEDEHFY VVDRYKELLK YKGSQVAPAE LEEILLKNPC IRDVAVVGIP DLEAGELPSA
              ▲       ▲   ▲                           ▲                ▲
                      *
          490        500        510        520        530        540
     FVVKQPGTEI TAKEVYDYLA ERVSHTKYLR GGVRFVDSIP RNVTGKITRK ELLKQLLVKA
```

GG

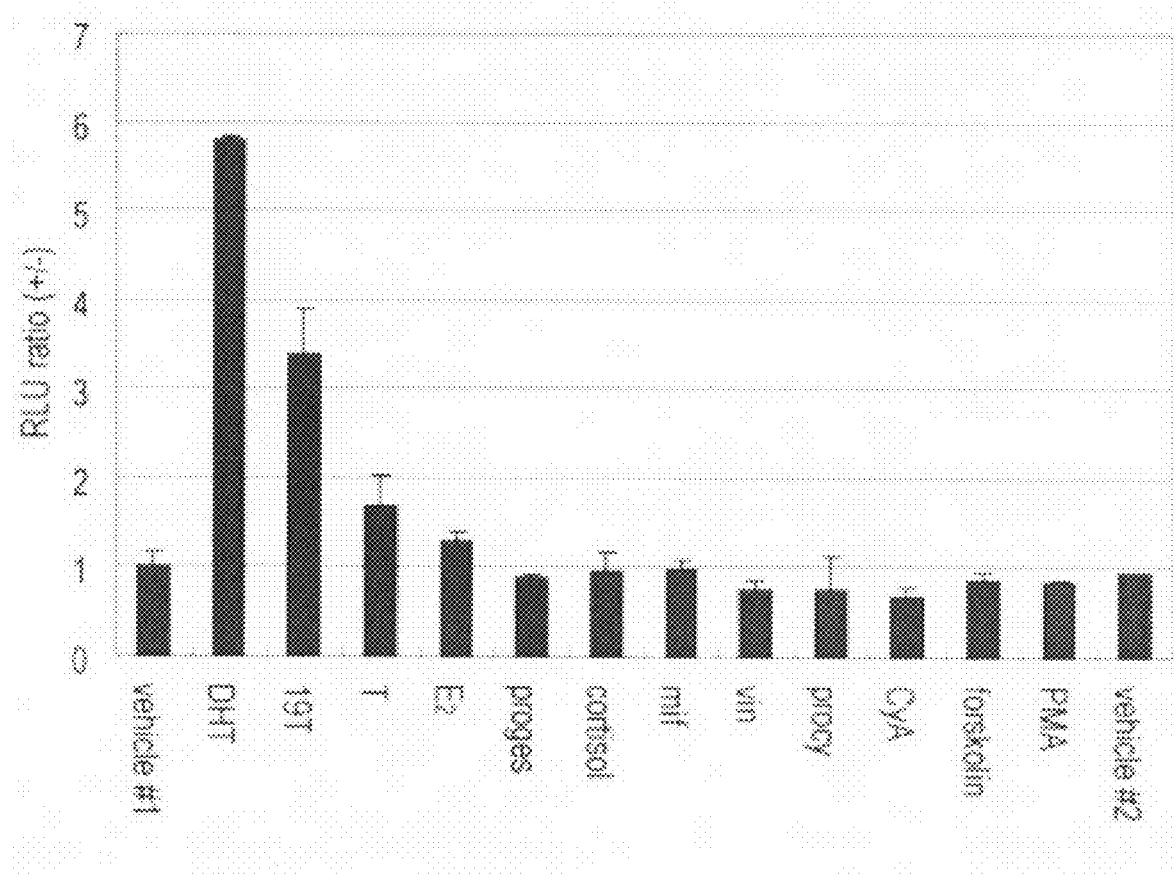

SINGLE MOLECULE-FORMAT BIOLUMINESCENT PROBE

This application is a U.S. national stage of International Application No. PCT/JP2008/050370 filed Jan. 15, 2008.

TECHNICAL FIELD

The present invention relates to a single molecule-format bioluminescent probe for detecting a ligand specific to a target protein.

Nuclear hormone receptors (NRs) functions as a ligand-activated transcription factor to control reproduction, development and metabolism. Androgen receptor (AR) is a member of the nuclear hormone receptor super family. Before binding to a ligand (agonist), AR resides in the cytoplasm, where AR is sequestered by binding to a heat shock protein. The agonist-AR binding causes a conformational change in the AR that release heat shock protein and allows the AR to be translocated to the nucleus (Non-Patent Documents 1-5). The AR translocated to the nucleus then exerts various actions such as a transcription activation (genomic action), by binding to a response element on a target gene promoter.

Various genomic and non-genomic actions of NRs are initiated by the conformational change in the ligand binding domain (LBD) and subsequent intra-molecular association between the LBD and the N-terminal domain (NTD) of NR. Such an intra-molecular association is observed in various NRs including AR, estrogen receptor (ER), progesterone receptor (PR) and glucocorticoid receptor (GR) (Non-Patent Documents 4 and 6).

The present inventors earlier proposed an application of nuclear trafficking of AR and GR as an index for determining hormonal activity of ligands (Non-Patent Documents 5, 8). The approach based on a nuclear trafficking of NRs demonstrated a great potential for exploring ligand-induced protein dynamics in a physiological context of living cells. However, the method requires for about 2 h for the splicing reaction to terminate in mammalian cells. Another disadvantage is that it cannot be used repetitively due to the irreversible mechanisms of the assay.

Another representative method for determining hormonal activities of ligands is a reporter-gene assay, of which reporters include GFP, β-galactosidase, and luciferases. This method inevitably requires a long ligand-stimulation time until the reporter enzymes are accumulated enough to be determined in living cells. Such a long determination time (actually about one day to complete the measurement) has hampered general applications of the methods to a ligand-induced short time kinetics and temporal dynamics of protein-protein interactions inside living cells. In addition, it is difficult with these prior art methods to discriminate whether the NR-binding ligand is an agonist or an antagonist.

The present inventors have previously proposed a method for determining an ligand-dependent association of NR's LBD with a coactivator peptide (LXXLL peptide) based on a fluorescence resonance energy transfer (FRET) technique (Patent Document 1, Non-Patent Document 7). In this method, a single-molecule format (single-chain) probe, which is an LBD/LXXLL peptide sandwiched between two chromophores having different fluorescent wavelengths, is expressed in a living cell. When an exogenous ligand (agonist) binds to the LBD, the distance between the two chromophores are changed upon the interaction of the activated LBD with the LXXLL peptide, thereby occurring a fluorescence resonance energy transfer (FRET). Since the FRET occurs immediately after the binding of LBD with the LXXLL peptide, the binding between the LBD and the ligand (agonist) can be detected immediately. It is also possible to specify an antagonist for the NR, which exerts an inhibitory effect on the FRET developed by the binding between the LBD and the agonist.

In addition to the relationship between the nuclear receptor (NR) and the ligand, other interactions of various substances with their respective target molecules in a living cell can be estimated. For example, cyclic guanosin monophosphate (cGMP), which is an intracellular second messenger functions as a signaling molecule in various biochemical processes (for example, circulatory myocyte relaxation, reticular photo-transmission, epithelial electrolyte transportation, bone growth, neuron activation), can be determined upon binding to its target molecule cGMP-binding protein (for example, cGMP-dependent protein kinase Iα:PLGIα). In addition, a lipid second messenger inositol-1,4,5-triphosphate (IP3) can be measured, that controls a number of biological responses including ertilization, morphogenesis, angiogenesis and neurological functions by inducing the release of $Ca^{2+}$ into the cytoplasm upon binding to an IP3 receptor ($Ca^{2+}$ channel) on a smooth-surfaced endoplasmic reticulum or sarcoplasmic reticulum membrane.

Such a substance as binding a specific target molecule is also referred to as a "ligand", and is a subject of the present invention. The present inventors have proposed a probe for visualizing the binding of the cGMP to its target molecule (cGMP-binding protein) based on the FRET technique (Patent Document 2), and a probe for visualizing the IP3 by utilizing the FRET technique (Patent Document 3). The present inventors have also proposed a means for detecting a protein-protein interaction which is visualized with the luminescence/fluorescence intensity of a reporter molecule (luminescent enzyme or fluorescent protein) instead of the FRET technique, in which the N and C fragments of the reporter molecule are respectively ligated to two independent proteins, respectively, and the N and C fragments are reconstituted or complemented upon the interaction of the two proteins (two molecules-format probe: Patent Documents 4, 5).

Patent Document 1: International Publication WO2005/078119, pamphlet
Patent Document 2: JPA 2002-017359
Patent Document 3: International Publication WO2005/113792, pamphlet
Patent Document 4: International Publication WO2002/008766, pamphlet
Patent Document 5: International Publication WO2004/104222, pamphlet
Non-Patent Document 1:Gelmann, E. P. J. Clin. Oncol. 2002, 20, 3001-3015.
Non-Patent Document 2: Roy, A. K.; Tyagi, R. K.; Song, C. S.; Lavrovsky, Y.; Ahn, S. C.; Oh, T. S.; Chatterjee, B. Ann. NY Acad. Sci. 2001, 949, 44-57.
Non-Patent Document 3: Singh, S. M.; Gauthier, S.; Labrie, F. Curr. Med. Chem. 2000, 7, 211-247.
Non-Patent Document 4: Warnmark, A.; Treuter, E.; Wright, A. P.; Gustafsson, J. A. Mol. Endocrinol. 2003, 17, 1901-1909.
Non-Patent Document 5: Kim, S. B.; Ozawa, T.; Watanabe, S.; Umezawa, Y. Proc. Natl. Acad. Sci. U.S.A. 2004, 101, 11542-11547.
Non-Patent Document 6: Schaufele, F.; Carbonell, X.; Guerbadot, M.; Borngraeber, S.; Chapman, M. S.; Ma, A. A.; Miner, J. N.; Diamond, M. I. Proc. Natl. Acad. Sci. U.S.A. 2005, 102, 9802-9807.
Non-Patent Document 7: Awais, M.; Sato, M.; Lee, X. F.; Umezawa, Y. Angew. Chem. Int. Ed. 2006, 45, 2707-2712.

Non-Patent Document 8: Kim, S. B.; Ozawa, T.; Umezawa, Y. Anal. Chem. 2005, 77, 6588-6593.

Non-Patent Document 9: Paulmurugan, R.; Gambhir, S. S. Anal. Chem. 2005, 77(5), 1295-1302.

Non-Patent Document 10: Kaihara, A.; Kawai, Y.; Sato, M.; Ozawa, T.; Umezawa, Y. Anal. Chem. 2003, 75(16), 4176-4181.

Non-Patent Document 11: He, B.; Bowen, N. T.; Minges, J. T.; Wilson, E. M. J. Biol. Chem. 2001, 276, 42293-42301.

Non-Patent Document 12: Tyagi, R. K.; Lavrovsky, Y.; Ahn, S.C.; Song, C. S.; Chatterjee, B.; Roy, A. K. Mol. Endocrinol. 2000, 14, 1162-1174.

DISCLOSURE OF THE INVENTION

A probe for detecting an NR ligand based on FRET technique (Patent Document 1, Non-Patent Documents 6, 7) is superior to the others in that it enables a quich detection of a ligand and also an accurate discrimination of agonists and antagonists, as mentioned above. However, it still requires a large-scale instrument equipped with a sophisticated filter system for measuring the resonance energy transfer between the two chromophores with a high accuracy upon ligand-LBD interaction, and for minimizing influence by autofluorescence of the two chromophores. Also, as it allows observation of only few cells, the measures do not provide a representative readout.

On the other hand, a protein-protein interaction based on the chromogenic protein splicing or complementation of the divided reporter fragments (Patent Documents 4, 5, Non-Patent Documents 4, 5) can be determined on the basis of the presence or absence of the signal development by the reconstituted enzymatic activity of the reporter molecule, different from the conventional FRET methods measuring subtle changes in wavelength. Nevertheless, the methods strategically depend on the reconstitution between two independent reporter fragments respectively linked to proteins of interest (two molecule-format probe), where the two components should be equally introduced into the cells. Biased expression levels cause an inefficiency in the probe actions.

Also, for the reconstitution of the two separated reporter fragments, the fragments should be approximated sufficiently. The approximation is only guaranteed by a strong affinity between the proteins of interest respectively linked to the separated reporter fragments.

The prior art invention for detecting a ligand binding to a target protein with a fluorescent resonance energy transfer (Patent Document 1, Non-Patent Document 1) enables a quick detection of the intended ligand (agonist, antagonist) due to a single molecule-format probe, but comprises disadvantages in points of easy-to-use and cost efficiency since the high level of measurement accuracy is required. On the other hand, the methods based on the intermolecular reconstitution of the split reporter molecule (two molecules-format type, Patent Documents 4, 5) is easy to a signal measurement, but is considered to have only limited applications because number of protein pairs exerting strong-enough interactions between the split reporter fragments is limited (for example, protein-protein interaction) and because of the biased expression levels of the component fusion proteins.

Accordingly, it is highly required a measure that maximizes the conventional merits, while overcoming the disadvantages of the prior art described above.

The present inventors discovered a single-chain probe, where a conformational change of a target protein upon ligand binding exerts an intramolecular complementation of split reporter molecule (luminescent enzyme) flanked to the both ends of the target protein, and have completed the present invention.

The present invention therefore provides a single molecule-format bioluminescent probe for detecting a target-specific ligand in a living cell, which comprises, a ligand-binding molecule of which conformation is changed upon binding to the ligand, and an N-terminal polypeptide (N-LE) and a C-terminal polypeptide (C-LE) of a luminescent enzyme (LE), which are flanked to each end of the ligand-binding molecule, respectively, wherein the N-LE and the C-LE self-complement to generate a luminescent signal only upon binding of the ligand to the ligand-binding molecule.

One preferred embodiment of the probe is that the ligand-binding molecule is a fusion molecule having a ligand-binding domain (LBD) and an LBD-interacting domain that interacts with the LBD upon binding of the ligand to the LBD.

In another preferred embodiment, the ligand is a nuclear receptor ligand, an intracellular second messenger, a lipid second messenger, a phosphorylated amino acid residue or a G protein-binding receptor ligand.

A further preferred embodiment of the probe is that the LBD is of the nuclear receptor, and the LBD-interacting domain is a coactivator peptide for the nuclear receptor, and the LBD is of an androgen receptor (AR) (AR LBD) and the coactivator peptide is a peptide comprising AR N-terminal 'FQNLF' motif (FQNLF (SEQ ID NO: 28) peptide) or a peptide comprising a *Xenopus* TIF2 'LXXLL' motif (LXXLL peptide).

In the most preferred embodiment of the probe in the present invention, the sequence order of the single molecule-format bioluminescent probe is N-LE/AR LBD/'FQNLF (SEQ ID NO: 28)' or 'LXXLL' peptide/C-LE.

The present invention also provides an expression vector capable of expressing any of the probes described above in a living cell.

In addition, the present invention provides a ligand detection kit comprising any of the probes described above or the expression vector described above and a substrate for the LE.

The present invention also provides a method for screening an unknown agonist to LBD, comprising:

(1) introducing any of the probes described above into a living cell;

(2) making a candidate substance to coexist with the living cell; and (3) identifying as an intended substance a candidate substance generating a luminescence from the living cell.

The present invention provides a method for screening an unknown antagonist which inhibits the binding of a known ligand with an LBD, comprising:

(1) introducing any of the probes described above into a living cell;

(2) making an antagonist candidate substance to coexist with the living cell;

(3) making a known agonist to coexist with the living cell; and (4) identifying as an intended substance a candidate substance reducing a luminescence from the living cell.

In one preferred embodiment of each screening method described above, the probe is introduced into a living cell by expressing the cDNA in the expression vector in the living cell.

In each invention described above, the term "living cell" means a cultured cell retaining its natural functions or a eukaryotic cell present in an individual organism (yeast cell, insect cell or animal cell) that is, especially a mammalian cell including a human cell. A living cell includes a prokaryotic cell.

The term "ligand" means a substance capable of binding specifically to a target molecule in a living cell and of altering the function of the target molecule. For example, agonists or antagonists to receptor proteins (for example, nuclear receptors or G protein-binding receptors) are considered. The ligand is also second messengers that to molecules involved in intracellular signal transduction.

The term "ligand detection" means determining the presence or absence of a ligand, the quantity of a ligand, the activity level of a ligand and the like.

The term "splitting of a luminescent enzyme (LE)" means a division of one molecule of the luminescent enzyme into two inactive molecules (inactivating the any luminescence ability). The position of division is not necessarily near the center, and may be a position that enables reconstitution of the fragments into an active single molecule (luminescence emitting) as a result of complementation when the two fragmented LEs closely approximate each other.

The term "chimeric DNA" refers to a DNA comprising DNA (I) to DNA (IV) ligated in a tandem chain and capable of expressing a fusion molecule consisting of the component proteins (peptides).

The term "fusion molecule" refers to a molecule consisting of individual components (proteins, peptides) in tandem form, wherein the C and N terminals of each protein or peptide are consecutively ligated via peptide bonds. Each protein or peptide may be ligated via a "linker peptide" or the like.

The term "single molecule-format bioluminescent probe" refers to a probe constructed all components for visualizing the presence of a target-specific ligand as a single-chain form. The term "LBD" is an abbreviation of "ligand-binding domain", while the term "LE" is of "luminescent enzyme".

The disclosures of Patent Document 1 and Non-Patent Document 7 relating to the detection of NR-specific ligands (agonists, antagonists) and Patent Documents 4 and 5 relating to the reconstitution of divided luminescent enzymes are included in the present invention as a reference.

Other terms and concepts in the present invention wick be described in detail in the below sections. In principle, the terms are in accordance with the IUPAC-IUB Commission on Biochemical Nomenclature, or are based on the meanings of the terms that are customarily employed in the art. Various technologies employed to implement the invention can easily and reliably be invoked by those skilled in the art in reference to publications, except in the case of technologies whose source documents are indicated in particular. For example, the technologies of genetic engineering and molecular biology can be performed according to the methods described in the following publications:

J. Sambrook, E. F. Fritsch & T. Maniatis, "Molecular Cloning: A Laboratory Manual (2nd ed.)", J. Sambrook, E. F. Fritsch & T. Maniatis, Cold Spring Harbor Laboratory Press, Cold Spring Harbor, N.Y. (1989);

D. M. Glover et al., ed., "DNA Cloning", 2nd ed., Vol. 1 to 4, (The Practical Approach Series), IRL Press, Oxford University Press (1995);

Ausubel, F. M. et al., Current Protocols in Molecular Biology, John Wiley & Sons, New York, N.Y., 1995;

"Zoku Seikagaku Jikken Koza 1, Gene research method II", Ed. by the Japanese Biochemical Society, Tokyo Kagaku Dojin (1986);

"Shin Seikagaku Jikken Koza 2, Nucleic acids III (recombination DNA technologies)", edited by the Japanese Biochemical Society, Tokyo Kagaku Dojin (1992);

R. Wu ed., "Methods in Enzymology", Vol. 68 (Recombinant DNA), Academic Press, New York (1980);

R. Wu et al. ed., "Methods in Enzymology", Vol. 100 (Recombinant DNA, Part B) & 101 (Recombinant DNA, Part C), Academic Press, New York (1983);

R. Wu et al.-ed., "Methods in Enzymology", Vol. 153 (Recombinant DNA, Part D), 154 (Recombinant DNA, Part E), & 155 (Recombinant DNA, Part F), Academic Press, New York (1987).

The technologies of genetic engineering and molecular biology can also be performed according to the methods described in the references quoted therein, as well as methods that are substantially similar to or modified from such methods. Various proteins or peptides employed in the invention and the DNAs that encode these proteins and peptides are available from existing databases.

Effects of the Invention

The invention offers a new, convenient and accurate means of detecting a target-specific ligand as an index of the presence or absence of a signal. The probe has a single-chain structure, and can easily be introduced into a living cell via an expression vector encoding the probes, where individual components were integrated within a single molecule.

BEST MODE FOR CARRYING OUT THE INVENTION

The probe in the present invention consists basically of a ligand-binding molecule, and N-LE and a C-LE at both ends thereof.

While these individual components may be tandemly linked to form a single-chain probe, for the purposes of effectively introducing the probe into a living cell, the probe may be introduced as an expression product of an expression vector. The expression vector may be constructed by inserting a single-chained chimeric DNA in which the respective DNAs encoding individual components may be directly ligated, or indirectly ligated via DNAs encoding "linker peptides".

In this case, any of the known vectors (vectors for eukaryotic cells) can be employed as a basal vector for the probe expression without any particular limitation. It is also possible to incorporate any known tissue-specific promoter sequence to regulate the expression of the chimeric DNA (for example, expression in a certain tissue in an individual organism). The probe expression vector may be introduced into a cell also by any known transfection methods, such as microinjection or electroporation. Alternatively, a lipid-based intracellular introduction (such as BioPORTER (Gene Therapy Systems, the United States) or Chariot (Active Motif, the United States)) may also be employed.

The individual components of the probe are described below.

A ligand-binding molecule is capable of changing its conformation upon binding to a ligand to allow N-LE and C-LE flanked at both the ends to be approximated by self-complementation into an active LE. For example, when the ligand is an intracellular second messenger or a lipid second messenger, the ligand-binding molecule may be the second messenger binding domain.

For detecting a nuclear receptor-specific ligand, for example, the ligand-binding molecule may be a known LBD of the nuclear receptor. For detecting a phosphorylation of an amino acid residue or a G protein-binding receptor ligand, LDB may be a phosphorylated amino acid-binding domain or a G protein-binding receptor, respectively. As the LBD of nuclear receptors, for example, androgen receptor LBD (AR LBD) may be prepared by means of a genetic engineering or chemical synthesis based on the known full-length nucleotide sequence of human AR (GenBank/M27430), to obtain its LBD region (amino acid number 672 to 910). A glucocorticoid receptor LBD (GR LBD) may be prepared based on the full-length sequence of human GR (GenBank/P04150) to obtain its LBD region (amino acid number 527 to 777).

In addition, a peptide (LBD-interacting domain) is ligated to the LBD described above. The peptide further interacts (associates) with the LBD to which the ligand bound. For example, when a ligand (agonist) is bound to a nuclear receptor, the N-terminal domain (NTD) of the receptor bends to interact with its corresponding C-terminal region. For example, in cases of a ligand-activated nuclear receptor, such as androgen receptor (AR) or estrogen receptor (ER), 'LXXLL' motif or 'FQNLF' motif (SEQ ID NO: 28) of the NTD binds to coactivator pocket of the LBD (Non-Patent Documents 1 to 5). Accordingly, in order to detect a ligand for a nuclear receptor, the LBD-interacting peptide may be an amino acid sequence comprising an 'LXXLL' motif or 'FQNLF' motif (LXXLL peptide, FQNLF (SEQ ID NO: 28) peptide) of the receptor's NTD. In this regard, since AR LBD AF-2 pocket is known to interact more potently with an NTD 'FXXLF' motif than with a coactivator LXXLL motif (Non-Patent Document 11), it is preferable when detecting a ligand for androgen receptor (AR) to use the 'FQNLF' peptide (SEQ ID NO: 28) as the LBD-interacting peptide. Upon detection of phosphorylation of an amino acid residue or a G protein-binding receptor ligand, the substrate sequence for the phosphorylation-recognition domain and G protein for the G protein-binding receptor may be utilized as the LBD-interacting domain.

LE includes a known firefly luciferase (FLuc), *Renilla* (sea pansy) luciferase (RLuc), click beetle luciferase (CBLuc) or the like. The amino acid sequences and the nucleotide (cDNA) sequences of the LEs have been known (for example GenBank/AB062786 for FLuc, GenBank/AY258592.1 for CBLuc and the like). Based on these sequence data, DNA encoding the LE can be obtained by known methods. The position at which each LE is divided into two fragments can be selected appropriately with reference to the known data. For example, FLuc can be divided at the amino acid sequence position 437/438, according to Non-Patent Document 9 describing the conventional two molecule-format probes. For the single molecule-format probe in the following examples is, the preferred split position of FLuc is 415/416 position (FIGS. 2 and 3). In the case of RLuc, the luminescence intensity becomes most eminent when the fragments are reconstituted after the dissection at the amino acid sequence position 91/92, as described in Patent Document 5 and Non-Patent Document 10. Furthermore, in the case of a CBLuc, the fragmentation should be made at amino acid sequence positions 439/440 or 412/413, as shown in the following examples (FIG. 13). As the following examples also show, the N-terminal fragment and the C-terminal fragment of LE may be partly overlapped or deleted.

The respective components may be ligated in any order provided the LE fragments are located on both ends. In this regard, when using AR LBD and 'FQNLF' peptide (SEQ ID NO: 28) for detecting a ligand for AR, the N-LE is preferably ligated to the LBD while the C-LE should be ligated to the 'FQNLF' peptide (SEQ ID NO: 28), as described in the following examples. Typically, the probe construction is, from the N-terminal end, [N-LE/AR LBD/FQNLF (SEQ ID NO: 28) peptide/C-LE] or [C-LE/FQNLF (SEQ ID NO: 28) peptide/AR LBD/L-LE].

For making use of another ligand-target molecule binding model, the appropriate ligation orders may be employed in each case. The appropriate order can be verified, for example, by altering the order of each DNA fragment in a probe expression vector. The insertion of DNA fragments into an expression vector can easily be conducted by those skilled in the art, and the selection of an appropriate ligation order does not require any extraneous experiments or trial-and-error investigation.

In the probe of the present invention, the respective components may also be ligated via linker peptides. In particular, it is preferable to insert a flexible linker peptide (for example, a GS linker consisting of an iterative sequence of glycine and serine) between LBD and LBD-interacting peptide. The linker peptide exerts an appropriate margin for the approximation between LBD and LBD-binding peptide upon ligand stimulation. By inserting a similar linker peptide between LBD and LE fragment, or between the peptide and LE fragment, the reconstitution of the both fragments can be accomplished efficiently.

A method of determining a ligand using the probe of the present invention is described below with reference to FIG. 1. In FIG. 1, AR LBD is for LBD, 'FQNLF' peptide (SEQ ID NO: 28) (indicated as "N-term") is for LBD-interacting domain, and a firefly luciferase (split at the position 415/416: indicated as "FLuc-N" and "Flu-C") is for LE. The AR LBD and the N-term are ligated to each other via a GS linker. The order of ligation is, from the N-terminal end, [FLuc-N/AR LBD/GS linker/N-term/FLuc-C].

This probe [FLuc-N/Ar LBD/GS linker/N-term/FLuc-C] is in a linear conformation in the absence of an agonist (FIG. 1). When the agonist binds to AR LBD, the conformation of the probe is changed to allow the N-term peptide to interact with AR LBD. As a result, AR LBD-linked FLuc-N and N-term-ligated FLuc-C are approximated to each other, thereby the full-length FLuc being reconstituted by protein complementation. The full-length FLuc thus reconstructed generates a luminescent signal in the presence of a luciferin as a substrate for the luciferase.

Such a ligand-dependent conformational change of the probe is reversible, and the linear conformation is restored upon removal of the ligand from AR LBD. Since the binding of a ligand to its target molecule is generally transient, the probe expressed in a cell enables repetitive ligand detection.

The agonist screening method in the present invention is based on the principle as described above. That is, cDNA encoding the probe is introduced into a cell, where the probe is expressed and coexisted with a candidate substance in this cell (for example, the candidate substance added to the culture medium of the cell may be introduced into the cell by diffusion or endocytosis). When the candidate substance is an agonistic substance, then the substance exerts the intramolecular complementation of the LE fragments in the probe, resulting in the development of the luminescent signal.

On the other hand, when an antagonist binds to AR LBD, the probe does not change its conformation, or makes an unusual conformation change. Accordingly, using this probe, it is possible to screen for unknown antagonists against known agonists. For example, an antagonist candidate is introduced into a cell carrying the probe. A known agonist is then introduced and the luminescence intensity is measured. If the candidate substance has an antagonistic effect, the agonist binding site of LBD is occupied by the candidate substance, thereby inhibiting the subsequent agonist-LBD binding. The antagonist-LBD binding does not change the probe conformation. Thus, normal binding of the agonist to LBD is blocked by the antagonist, consequently causing no change in the conformation of the probe. In this case, no luminescent signal is observed, or the luminescence intensity is reduced when compared with the introduction of the agonist alone. On the other hand, when the candidate substance has no antagonistic effect, the candidate substance does not bind to LBD, and the subsequently supplemented agonist binds to the LBD, thereby exhibiting a high luminescent signal similar to a control.

Test substances to be subjected to the screening methods include organic or inorganic compounds (especially compounds with low molecular weight), proteins, peptides and the like. Such a substance may have a known or unknown function or structure. A "combinatorial chemical library" is a means that is useful as test substance group for efficiently identifying an intended substance. Preparation and screening of a combinatorial chemical library are well-known in the art (for example, see U.S. Pat. Nos. 6,004,617; 5,985,365). It is also possible to use commercially available libraries (for example, libraries available from ComGenex (the United States), Asinex (Russia), Tripos, Inc. (the United States), ChemStar, Ltd. (Russia), 3D Pharmaceuticals (the United States), Martek Biosciences and the like). It is also possible to conduct a so-called "high-throughput screening" by applying a combinatorial chemical library to a cluster of cells expressing the probes.

EXAMPLES

The present invention is described more specifically and in more detail in the following examples, in which the invention is not restricted in any way.

Example 1

Probe Having Firefly Luciferase (FLuc) as a Luminescent Enzyme (1) Methods
(1-1) Plasmid Construction The cDNAs of N-terminal (Fluc-N; 1-415 AA) and C-terminal (Fluc-C; 416-510 AA) domains of split FLuc were amplified to introduce each unique restriction site at both ends of the domains using adequate primers and a template plasmid carrying the full-length cDNA of Fluc. The cDNA-encoding AR LBD (672-910 AA) was modified by PCR to introduce adequate restriction sites at the both ends of the domains. DNA oligomers encoding an AR N-terminal motif (11 AA; SEQ ID NO: 1; $^{20}$RGAFQNLFQSV$^{30}$) and its alanine mutant (11 AA; SEQ ID NO: 30 $^{20}$RGAAQNLFQSV$^{30}$) were custom-synthesized by Exigen (Tokyo, Japan). The amplified fragments of each site were subcloned into the corresponding restriction enzyme-digested pcDNA 3.1 (+) vector backbone (Invitrogen). The constructed plasmids were sequenced to ensure fidelity with a BigDye Terminator Cycle Sequencing kit and a genetic analyzer ABI Prism310.

(1-2) Cell Culture and Transfection

Cervical carcinoma-derived HeLa cells were sub-cultured in 12-well plates in Dulbecco's modified eagle's medium (DMEM; Sigma) supplemented with 10% steroid-free fetal bovine serum (FBS) and 1% penicillin-streptmycin (P/S) at 37° C. in a 5% $CO_2$ incubator. HeLa cells in 12-well plates were transfected with pAR-NC, pAR-CN, or pAR-mut using a transfection reagent, TransIT-LT1 (Minis), which guarantees about 8% transfection efficiency to HeLa cells when incubated for 24 h. The cells were incubated for 12 h and then used for the following experiments.

(1-3) Western Blot

HeLa cells in a 6-well plate were transfected with pAR-CN, pAR-NC, or pAR-mut, and incubated for 16 h. The cells were washed once with PBS and lysed in 100 μL of a lysis buffer (1% SDS/10% glycerol/10% 2-mercaptoethanol/0.001% bromophenol blue/50 mM Tris-HCl, pH 6.8). An aliquot of the samples was electrophoresed in 10% acrylamide gels, transferred to nitrocellulose membrane, and blotted with mouse anti-FLuc antibody (Promega) or mouse anti-β-actin antibody (Sigma). The blots were incubated with horseradish peroxidase (HRP)-conjugated secondary antibody and finally visualized with a ECL chemiluminescence substrate kit (GE Healthcare).

(1-4) Determination of Androgenic Activity of Ligand

HeLa cells in 12-well plates were transfected with the plasmids and incubated for 16 h. The cells were then stimulated with various steroids or chemicals for 20 min. The recovered enzyme activities by ligands were estimated with a luminescence substrate kit, Bright Glo (Promega) or Dual-luciferase assay kit (Promega), according to the manufacturer's manuals. The brief procedure of the Bright Glo kit is as follows: The cells on the 12-well plates were transiently transfected with pAR-NC and washed with PBS. An 80 μL of substrate solution was added to each well of the plates. After a 3 min incubation at 37° C., the luminescence intensities from the cell lysates were recorded with a luminometer (Minilumat LB9506; Berthold). The protein amounts in the cell lysates were subsequently determined using a Bradford reagent for a normalization of the luminescence intensities. In specific, the firefly luminescence, which was normalized against the determined protein amount, was expressed as "RLU/protein (Bright Glo)". The unit means the firefly luminescence intensity from the 1 μg of cell lysate.

In case using a Dual-luciferase assay kit, the cells in the 12-well plates were cotransfected with pAR-NC and pTK-RLuc (Promega). pTK-RLuc expresses a full-length Renilla luciferase (RLuc), which is inserted for an internal reference to the transfection efficiency. The cells were stimulated with a ligand for 20 min, and then washed once with PBS. They were subjected to a lysis buffer and incubated for 15 min. The lysates were transferred to test tubes and mixed with the specific substrate solution from the kit. The developed luminescence intensities were read for the first 20 sec with the luminometer. After quantifying the firefly luminescence ($L_F$), the activity of FLuc was quenched, and Renilla luminescence ($L_R$) as an internal reference was measured using the specific substrate solution for another 20 sec. The firefly luminescence normalized against the Renilla luminescence was termed as "RLU ratio (Dual)"; i.e., $L_F/L_R$.

(1-5) Time-Course of the Responses

HeLa cells cultured in a 12-well plate were transfected with pAR-NC. The cells were harvested and were equally divided into two test tubes. The cells in each test tube were suspended with a 100 μL luciferin substrate solution. Soon after the substrate addition, the luminescence intensities of respective test tubes were monitored over a 1-min time period with the luminometer. Five minutes after the substrate addition, an aliquot of DMSO or 5α-dihydroxytestosterone (DHT) was supplemented to respective tubes to be 0.1% DMSO (final conc) or $10^{-6}$ M DHT (final conc). The luminescence intensities from each test tube were then monitored for another 15 min.

(1-6) Determination of Inhibitory Effects of Androgen Antagonists

Inhibitory effects of various androgen antagonists on the DHT-induced luminescence intensities were tested with the HeLa cells carrying pAR-NC and pTK-RLuc. HeLa cells were transfected with pAR-NC and pTK-RLuc, and extensively incubated for 16 h. The HeLa cells in each well were pre-stimulated with 0.1% DMSO or $5\times10^{-4}$ M of antagonists, vinclozolin, procymidone, CPA, or flutamide for 20 min. All the cells except for a control were then additionally stimulated with $10^{-5}$ M DHT for 20 min. The luminescence intensities of each well were determined with a Dual-luciferase assay kit (Promega).

(1-7) Reversibility Test of the Luminescent Probe

Reversibility of the luminescence intensities of the present luminescent probe was estimated by a DHT treatment and its withdrawal. The HeLa cells cultured in a 12-well plate were transfected with pAR-NC. After the incubation for 16 h, the cells in the plate wells were stimulated with $10^{-5}$ M DHT for 20 min. Then the medium in the plate wells was replaced with a fresh DMEM supplemented with 10% steroid-free FBS and 1% P/S. At 0.5, 1, 2, and 4 h after the medium change, the luminescence intensities were respectively determined with a Bright Glo assay kit (FIG. 9).

The alteration of luminescence intensities by a DHT treatment and subsequent withdrawal of the DHT was measured using a Dual-luciferase assay kit (FIG. 10). HeLa cells raised in 12-well plates were transfected with pAR-NC. The plate wells were divided into five sections, each section of which consisted of three wells. All the cells in the four sections except for a control section (vehicle addition; treatment [0]) were stimulated with $10^{-5}$ M DHT for 20 min. The cells in a first section were harvested and the luminescence intensities were determined (treatment [1]). And then the medium of the other three sections were replaced with a fresh DMEM supplemented with 10% steroid-free FBS and 1% P/S and incubated for 20 min. The decreased luminescence intensities were sampled from one of the three sections (treatment [2]). The cells in the remained two sections were then stimulated again with $10^{-5}$ M DHT for 20 min. One of the remaining two sections was then harvested for the determination of the luminescence intensities developed by the secondary DHT addition (treatment [3]). The medium of the remained last section was replaced with a new fresh DMEM supplemented with steroid-free FBS and P/S, and incubated for 20 min. The luminescence intensities from the cells were recorded (treatment [4]).

(2) Results and Discussion (2-1) Comparison of the Androgen Sensitivity of the Three Indicators Constructed As specified in FIG. 2, three kinds of plasmids were constructed in the present study. pAR-CN and pAR-NC differ in the sequence of FLuc-N and -C domains, but contain the same 'FQNLF' motif (SEQ ID NO: 28). pAR-mut with an alanine mutant of the 'FQNLF' motif (SEQ ID NO: 28) was also constructed for examining whether the luminescence intensities of the present study is indeed from the interaction of AR LBD with the 'FQNLF' motif (SEQ ID NO: 28).

The absolute luminescence intensities among the HeLa cells carrying the three plasmids were respectively compared before and after the addition of DHT (FIG. 3. A stimulation of the cells carrying pAR-NC with $10^{-5}$ M DHT induced eight times higher luminescence intensities than a vehicle (0.1% DMSO) stimulation did. On the other hand, the cells carrying pAR-mut exhibited four times weaker luminescence intensities than the cells carrying pAR-NC with the same DHT stimulation. The results are due to that a point mutation from the 'FQNLF' motif (SEQ ID NO: 28) to the 'AQNLF' motif (SEQ ID NO: 31) weakened the association between AR LBD and 'FQNLF' motif (SEQ ID NO: 28). With a withdrawal of the agonist, AR LBD releases the 'FQNLF' motif (SEQ ID NO: 28), and thus the probe loses the luciferase activities. This result demonstrates that the intra-molecular interaction of AR LBD with 'FQNLF' motif (SEQ ID NO: 28) was the reason for the reconstitution of the bioluminescence by the present probe.

Among the cells transfected with the three kinds of probes, the cells carrying pAR-CN showed the weakest luminescence intensities upon stimulated with a $10^{-5}$ M DHT. The subsequent western blotting with an anti-FLuc antibody showed that a similar amount of the probes were expressed from pAR-CN, pAR-NC and pAR-mut (FIG. 3). The weak luminescence intensity by the probe from pAR-CN may be caused by a mismatch between the N- and C-terminal fragments of split-FLuc due to the different linker lengths or a steric hindrance among the protein domains that interfere with the protein complementation of the N- and C-terminal fragments.

(2-2) Western Blotting for Determining the Expression of the Genetic Indicators

A western blotting study was performed to determine 1) whether the fusion proteins are expressed and 2) how much amount of the fusion proteins is expressed. The results are shown in FIG. 4. HeLa cells carrying pAR-CN (lane 2), pAR-NC (lane 3), or pAR-mut (lane 4) in addition to the mock-transfected cells as a negative control (lane 1) were electrophoresed in 10% acrylamide gel and transferred to a nitrocellulose membrane. Mouse anti-AR antibody (Santa Cruz) recognized specific bands of 92 kDa, the size of which was the same as that of the expected fusion proteins. Similar band thicknesses were observed between lane 2, 3 and 4, which indicates that the same amounts of the fusion proteins were expressed from the plasmids, pAR-CN, pAR-NC, and pAR-mut. The similarity in the expression efficiency between the plasmids suggests that the differences in the luminescence intensities seen in FIG. 3 were not caused by the differences in the amount of the probe proteins, but by the probe performance in sensing ligand activities.

(2-3) The Androgen-Dependent Kinetics in the Luminescence Intensities from pAR-NC The DHT-induced luminescence intensities from the HeLa cells carrying pAR-NC were monitored over a 1-min time course (FIG. 5). The cells quickly increased the luminescence intensities upon stimulated with DHT, and they reached to a plateau after 9 min. This kinetics demonstrates that 9 min is required for a androgen-AR LBD binding and subsequent full association of AR LBD with 'FQNLF' motif (SEQ ID NO: 28). A previous FRET-based study for androgen actions demonstrated that 7 min is required for an androgen-induced intramolecular folding of AR. The difference of the observed response time between the two methods may be due to a difference in the experimental setup: i.e., the FRET-based study used a full-length AR in the fluorescence probe, whereas a net 'FQNLF' motif (SEQ ID NO: 28) was used in the present luminescence study. The present probe exhibited an extremely high signal-to-background ratio up to around 20 times over the baseline intensities. The high sensitivity of the present probe may be due to the intrinsic characteristics of luminescence, which is free from background fluorescence, i.e., low background intensity. Another reason for the high signal-to-background ratio may be the optimized molecular structure for the FLuc complementation and the superiority of the present dissection point of FLuc over others.

(2-4) Determination of the Androgenic Activities of Steroid Hormones and Synthetic Chemicals The dose-dependent curves for the concentrations of steroid hormones vs. luminescence intensities were determined (FIG. 6). The HeLa cells carrying pAR-NC were stimulated for 20 min with the steroid hormones, 5α-hydroxytestosterone (DHT), testosterone (T), 19-nortestosterone (19T), or 17'-estradiol ($E_2$). The subsequent luminescence intensities were developed with a Dual-luciferase assay kit. The ligand selectivity was as follows in the decreasing order: DHT>19T>T>$E_2$>vehicle (0.1% DMSO). The 50% effective concentration ($EC_{50}$) of DHT was $3.9 \times 10^{-6}$ M, and the detection limits were around $10^{-7}$ M. The results demonstrate that 1) the present molecular probe can discriminate different steroids with a high sensitivity, and 2) it provides a high-throughput determination of the activities of steroids, generally within 20 min.

In addition, agonistic activities of various steroids and synthetic chemicals at $10^{-5}$ M were compared using the HeLa cells carrying pAR-NC (FIG. 7). DHT and testosterone (T) at $10^{-5}$ M efficiently increased the luminescence intensities of 15 and 5 times higher than that of the control (0.1% DMSO), respectively. On the other hand, the other steroids and synthetic chemicals did not induce distinct luminescence intensities from the HeLa cells carrying pAR-NC at their $10^{-5}$ M. Flutamide and cyproterone acetate (CPA) did not show any androgenic activities in the present study, although the chemicals were previously reported to have agonistic activities for AR nuclear trafficking (Non-Patent Document 5). The disagreement between the present and previous methods can be explained as their intrinsic differences in the determination strategy, i.e., they are respectively established based on a different signaling pathway.

(2-5) Inhibitory Effects of Synthetic Chemicals on the Agonistic Activity of DHT Several synthetic chemicals known as antagonists were tested for their antagonic effects against the androgenic activity of DHT (FIG. 8). Among the chemicals, CPA is a known steroidal antagonist for AR, whereas vinclozolin, procymidone, and flutamide are non-steroidal antagonists for AR. HeLa cells carrying pAR-NC were first stimulated with $5 \times 10^{-4}$ M of respective antagonists for 20 min, and then with $10^{-5}$ M DHT for another 20 min. All the chemicals exhibited antagonistic activities to the luminescence intensities developed by DHT. The antagonistic effects of the chemicals were ranked as follows in the decreasing order: flutamide (78%) >CPA (73%)>procymidone (68%)>vinclozolin (57%). The numbers in parenthesis represent the percentage inhibition of the DHT-induced luminescence after exposure of the respective antagonists for 20 min.

The inhibition study proved that the development of luminescence intensities in the present probe is indeed caused by ligand-controlled actions of AR LBD, i.e., the conformational change of AR LBD and the following association of AR LBD with 'FQNLF' motif (SEQ ID NO: 28). The results also suggest that the present method is useful for a high throughput screening for prostate cancer drugs (androgen antagonist) among candidates (2-6) Reversibility of the Luminescence Intensities from the Probe in Response to Androgen The ligand-controlled dynamics of the AR LBD-'FQNLF' motif (SEQ ID NO: 28) association was explored by determining the luminescence intensities after androgen treatment and withdrawal (FIGS. 9 and 10).

First, HeLa cells carrying pAR-NC were stimulated with $10^{-5}$ M DHT for 20 min. The medium was then replaced with a fresh steroid-free medium. At 0.5, 1, 2, and 4 h after DHT withdrawal, the luminescence intensities at each time point were monitored (FIG. 9). At 0.5 and 1 h after the medium replacement, the luminescence intensities were quickly decreased to 26 and 11% of the intensities before the medium change, respectively. At 2 h after the medium replacement, the luminescence intensities were decreased to the baseline. The results demonstrate that 1) the time attaining a half maximum luminescence intensities ($t_{1/2}$) after the hormone withdrawal is around 20 min, and 2) the complete removal of DHT from the probe requires 2 h.

Next, the changes on the luminescence intensities by a repeated treatment and withdrawal of androgen were monitored (FIG. 4(B)). A 20 min stimulation with $10^{-5}$ M DHT induced 15 times higher luminescence intensities than that of the vehicle (0.5% DMSO) (treatment [1]). Subsequent androgen withdrawal by a medium change decreased the luminescence intensities to 39% of the initial intensities by the androgen treatment in 20 min (treatment [2]). The second androgen treatment with $10^{-5}$ M DHT recovered the luminescence intensities to 96% of the initial intensities by $10^{-5}$ M DHT (treatment [3]). The following androgen withdrawal decreased the luminescence intensities down to 40% of the initial intensities by $10^{-5}$ M DHT (treatment [4]). The results show that 1) the present AR fusion proteins preserve basic functional activities even with a repeated androgen treatment and withdrawal, and 2) around 20 min is required until a half withdrawal of DHT from the AR LBD in HeLa cells.

Previously, a ligand-controlled dynamics of AR was studies with a GFP-linked full-length AR (Non-Patent Documents 2 and 12). The studies exhibited that 1) AR is translocated into the nucleus within 15~60 min, 2) AR is recycled, and 3) AR is returned to cytosol 4 h after the androgen withdrawal. Here, the response times of the present luminescent probe were found to be as follows: 1) 9 min for the association of AR LBD with 'FQNLF' motif (SEQ ID NO: 28) in NTD, 2) 2 h for the complete withdrawal of androgen from AR LBD, and 3) the half-time ($t_{1/2}$) for the withdrawal of DHT from AR LBD is about 20 min.

Taken together, it was concluded that a new genetically encoded bioluminescent probe was developed for determining androgenic activities of ligands based on a ligand-induced intra-molecular conformational change of AR. FLuc was dissected into N- and C-terminal fragments, where the activities were completely lost. AR LBD fused with 'FQNLF' motif (SEQ ID NO: 28) was inserted between the N- and C-terminal fragments of FLuc. Androgen-induced association of AR LBD with the 'FQNLF' motif (SEQ ID NO: 28) of the NTD resulted in the complementation of N- and C-terminal fragments of split-FLuc, which is followed by a subsequent recover of FLuc activities. The present genetic indicator is characterized as a single molecule-format bioluminescent probe incorporating all the components required for recognizing cellular signaling and emitting bioluminescence in a single probe molecule. With the present method, we explored androgenic activities of ligands as well as the selectivity and detection limit of the probe upon AR hormone-induced conformational changes of AR LBD in HeLa cells. Although this study exemplified an intra-molecular conformational change of AR LBD, any intra-molecular conformational change of NRs could be imaged with the present molecular imaging scheme using a singular molecule-format probe. Considering that ligand-induced conformational changes of NR LBD are an initial trigger of ligand-regulated genomic and nongenomic actions of NRs, the present method is generally applicable for detecting cellular or pharmacological events that specifically inhibit or enhance a ligand-induced conformational change of NRs.

Example 2

Single Molecule-Format Luminescent Probe with a Click Beetle Luciferase (CBLuc)

Probe-expression plasmids were constructed by subcloning chimeric DNAs of FIG. 11 into pcDNA 3.1(+) vector. Each of these plasmids was named as pSimbe (Single Molecule-format probe using a click Beetle). They have an AR LBD and various LBD-interacting peptide, i.e., pSimbe-FQ has 'FQNLF' motif (SEQ ID NO: 28) ($^{20}$RGAFQNLFQSV$^{30}$; SEQ ID NO: 1) derived from human AR NTD, pSimbe-LXP has forward sequence of 'LXXLL' motif ($^{686}$KHKILHRLLQDSS$^{698}$; SEQ ID NO: 2) and pSimbe-LXA has a reverse sequence of 'LXXLL' motif ($^{698}$SSDQLLRHLIKHK$^{686}$; SEQ ID NO: 3) from Xenopus TIF2. The amino acid sequences of N-terminal (CBLuc-N) and C-terminal (CBLuc-C) of CBluc are as in FIG. 11, respectively. The combination of [A] and [a] corresponds to Plasmid [1], and Plasmids [2], [3] to [10] are provided in a corresponding manner. FIG. 12 shows a full-length CBLuc amino acid sequence in which the arrows indicate the cleavage sites in plasmids [1] to [7]. In plasmids [8] to [10], the CBLuc-N and the CBLuc-C are partly overlapped or deleted. The asterisk indicates cleavage site (439/440) in Plasmid [3].

Table 1 shows PCR primers for amplifying each DNA. Bold letters indicate the restriction sites, while underlined letters indicate initiation codons and termination codons. Italics are GS linker codons.

TABLE 1

| Primer name | Primer sequence(5' → 3') | SEQ ID NO: | binding position to template |
|---|---|---|---|
| CBLuc-N fragments | | | |
| Fwd_Hind_1 | TTTAAGCTTACCGCC<u>ATG</u>GTAAAGCGTGAGAAAAATGTCATC | SEQ ID NO: 4 | 1-27 |
| Bwd_Kpn_1 | AAAGGTACCGCCTCCTGCCAGCTCGCCCACTTGGTTCGGGCC | SEQ ID NO: 5 | 1138-1161 |
| Bwd_Kpn_2 | AAAGGTACCGCCTCCTGCGTAAAAATGCTCATCTTCGTCGTA | SEQ ID NO: 6 | 1267-1290 |
| Bwd_Kpn_3 | AAAGGTACCGCCTCCTCCGATCAGCTCCTIGTAACGATCCAC | SEQ ID NO: 7 | 1294-1317 |
| Bwd_Kpn_4 | AAAGGTACCGCCTCCTCCATCGCGAATGCATGGATTTTTCAA | SEQ ID NO: 8 | 1366-1389 |
| Bwd_Kpn_5 | AAAGGTACCGCCTCCTCCAGCAGAAGGCAGTTCGCCGGCCTC | SEQ ID NO: 9 | 1417-1440 |
| Bwd_Kpn_6 | AAAGGTACCGCCTCCTCCGTCGTCGTCGATGGCCTCCTTGGT | SEQ ID NO: 10 | 1213-1236 |
| Bwd_Kpn_7 | AAAGGTACCGCCTCCTCCCTTGTATTTGATCAGCTCCTTGTA | SEQ ID NO: 11 | 1303-1326 |
| CBLuc-C fragments | | | |
| Fwd_Bam_1 | TTTGGATCCGGAGGCGGCTGTATCAAAGGCCCTATGGTGAGC | SEQ ID NO: 12 | 1162-1185 |
| Fwd_Bam_2 | TTTGGATCCGGAGGCGGCGTCGTGGATCGTTACAAGGAGCTG | SEQ ID NO: 13 | 1291-1314 |
| Fwd_Bam_3 | TTTGGATCCGGAGGCGGCAAATACAAGGGTAGCCAGGTTGCT | SEQ ID NO: 14 | 1318-1341 |
| Fwd_Bam_4 | TTTGGATCCGGAGGCGGCGTCGCTGTGGTGGGCATTCCTGAT | SEQ ID NO: 15 | 1390-1413 |
| Fwd_Bam_5 | TTTGGATCCGGAGGCGGCTTCGTTGTCAAGCAGCCTGGTACA | SEQ ID NO: 16 | 1441-1464 |
| Fwd_Bam_6 | TTTGGATCCGGAGGCGGCGGCTGGTTGCATTCTGGTGATTTT | SEQ ID NO: 17 | 1237-1260 |
| Fwd_Bam_7 | TTTGGATCCGGAGGCGGCGGTAGCCAGGTTGCTCCAGCTGAG | SEQ ID NO: 18 | 1327-1350 |
| Fwd_Bam_8 | TTTGGATCCGGAGGCGGCGAGCTGATCAAATACAAGGGTAGC | SEQ ID NO: 19 | 1309-1332 |
| Bwd_Xho_1 | AAATTTCTCGAG<u>CTA</u>ACCGCCGGCCTTCACCAACAA | SEQ ID NO: 20 | 1606-1629 |
| Binding motifs (FXXLF or LXXLL) | | | |
| ARn_SalBam_F | TATGAATTCGTCGACGGCGGCAACGGCG-GCCGAGGAGCTTTCCAGAATCTGTTCCAGAGCGTGGGATCCTTA | SEQ ID NO: 21 | 20-30 (AR NTD) |
| ARn_SalBam_B | TAAGGATCCCACGCTCTGGAACAGAT-TCTGGAAAGCTCCTCGGCCGCCGTTGCCGCCGTCGACGAATTCATA | SEQ ID NO: 22 | 30-20 (AR NTD) |
| TIF_par_Not-Bam_F | AAAGTCGACGGCGGCCGCAAGCAT-AAAATTTTGCACAGACTCCTTCAGGACAGTAGTGGATCCTTT | SEQ ID NO: 23 | 2026-2064 (TIF2) |
| TIF_par_Not-Bam_B | AAAGGATCCACTACTGTCCTGAAG-GAGTCTGTGCAAAATTTTATGCTTGCGGCCGCCGTCGACTTT | SEQ ID NO: 24 | 2064-2026 (TIF2) |
| TIF_ant_Not-Bam_F | AAAGTCGACGGCGGCCGCAGTAGTGAC-CAGCTTCTCAGACACTTGATTAAACATAAGGGATCCTTT | SEQ ID NO: 25 | 2026-2064 (TIF2) |
| TIF_ant_Not-Bam_B | AAAGGATCCCTTATGTTTAATCAAGT-GTCTGAGAAGCTGGTCACTACTGCGGCCGGCGTCGACTTT | SEQ ID NO: 26 | 2064-2026 (TIF2) |

(1) Determining Digestion Sites of CBLuc

Using each of pSimbe-FQs [1] to [10] and the consequently recovered luminescent intensities after stimulation of $10^{-5}$ M DHT, an appropriate digestion site of CBluc for the single molecule-format probe was investigated. The results are shown in FIG. 13, in which plasmids [3], [6], [9] and [10] exhibited marked increases in the luminescence intensity versus the background.

(2) Study on Binding Ability of AR LBD with Each Interacting Peptide

The plasmids pSimbe-FQ, pSimbe-LXP and pSimbe-LXA were transfected in HeLa cells for probe expression, and the binding ability of the AR LBD and peptides known to interact therewith was compared in the presence and absence of $10^{-5}$ M DHT. The digestion site of the CBLuc was similar to that in plasmid [3] described above.

The results are shown in FIG. 14, which indicates that while all peptides underwent binding to AR LBD, a probe carrying 'FQNLF' motif (SEQ ID NO: 28) of human AR exhibited a significant increase in the luminescence intensity compared to the background.

(3) Relative Comparison of the Binding Strength of LXXLL Motif with AR LBD or GR LBD Four plasmids were constructed by using AR LBD and a GR LBD as representatives of the LBD, and the reverse sequence and the forward sequence of 'LXXLL' motif as interacting peptides; pSimbe-LXP encoding AR LBD with the forward sequence of 'LXXLL' motif; pSimbe-LXA encoding AR LBD with the reverse sequence of 'LXXLL' motif; pSimbe-GRP encoding GR LBD with the forward sequence of 'LXXLL' motif; and pSimbe-GRA encoding GR LBD with the reverse sequence of 'LXXLL' motif. The digestion site of CBLuc was similar to that in plasmid [3] described above. These plasmids were expressed in MCF-7 cells, and the consequent luminescence intensities of the luminescence from the probes were compared in the presence and absence of $10^{-5}$ M DHT.

The results are shown in FIG. 15. While both the forward and reverse sequence of 'LXXLL' motifs bound strongly to AR LBD, the anti-parallel binding between the forward sequence of 'LXXLL' and AR LBD was especially strong. (The binding occurs in an anti-parallel form because of the intramolecular binding in a single molecule.)

(4) Study on Ligand Selection in Cell Lines

Four cell lines, MCF-7 (human breast cancer cell), CHO (Chinese hamster ovary cell), HeLa (human cervical carcinoma cell) and NIH 3T3 (mouse fibroblast cell) were transfected with pSimbe-LXA-expressing plasmids. The cells were stimulated with each $10^{-5}$ M 17β-estradiol ($E_2$), testosterone (T) and DHT for 20 minutes, and luminescence intensities were measured.

The results are shown in FIG. 16. In all of the cells, the pSimbe-LXA exhibited a marked increase in the luminescence intensity versus the background, but the intensity from the MCF-7 cells was especially pronounced.

(5) Study on Probe Expression

MCF-7 cells were transfected with the expression plasmids pSimbi[3], pSimbe-LXP and pSimbe-LXA, and the respective probe expression was analyzed by western blotting.

The results are shown in FIG. 17, which indicates that all probes were expressed in the cells.

(6) Dose-Response Curve of Various Steroid Hormones on Luminescence Intensities from pSimbi Probes MCF-7 cells were transfected with plasmids pSimbi[3] and pSimbe-LXA, and stimulated with a series of different concentrations of either DHT, 19T (19-nortestosterone), T or $E_2$ to measure the luminescence intensities (FIG. 18).

The results are shown in FIG. 18. All probes exhibited dose-dependent increases in the luminescence intensity in response to the DHT stimulation.

(7) Antagonist Assay

MCF-7 cells were transfected with plasmid pSimbe-LXA to examine the inhibitory effect of CPA (cyproterone acetate) on the $10^{-6}$ M DHT-induced probe luminescence.

The results are shown in FIG. 19, and indicate that the association of AR LBD with 'LXXLL' motif in MCF-7 cells was inhibited by CPA at concentrations 10 times and 100 times that of DHT.

(8) Time-Course of the Luminescence Intensity of pSimbe Probe after DHT Stimulation MCF-7 cells were transfected with plasmid pSimbe-LXA to examine the time-course of the DHT concentration-dependent luminescence intensity.

The results are shown in FIG. 20, and indicate a marked change in the luminescence intensity over time even with $10^{-5}$ and $10^{-6}$ M DHT stimulations.

(9) Repetitive Measurement of pSimbe Probe

MCF-7 cells were transfected with plasmid pSimbe-LXA, and stimulated two times with $10^{-5}$ M DHT for 20 minutes followed by DHT removal with medium replacement, in which the change in the luminescence intensity was monitored.

The results are shown in FIG. 21. The plasmid pSimbe-LXA exhibited reversible recovery in the luminescence intensities even after the second DHT stimulation.

(10) Measurement of the Androgenic Hormone Activity of Various Ligands

MCF-7 cells were transfected with plasmid pSimb-LXA, and the luminescence intensity upon stimulation with each of DHT, 19T, T, $E_2$, progesterone (proges), mifepristone (Mif; RU486), vinclozolin (vin), procymidone (procy), cyproterone acetate (CPA) and phorbol 12-myristate 13-acetate (PMA) were measured. As controls, vehicle #1 (0.1% DMSO) and vehicle #2 (0.02M phosphoric buffer saline (PBS)) were tested.

The results are shown in FIG. 22. Since the probe from plasmid pSimbe-LXA exhibited a significantly potent luminescence upon stimulation with DHT and 19T, the androgenic hormone activity of these ligands was confirmed.

BRIEF DESCRIPTION OF THE DRAWINGS

FIG. 10 is determination of the reversibility of the luminescence intensities from the probe in response to androgen in Example 1. Stimulation and withdrawal of $10^{-5}$ M DHT were repeated as specified in section A. The luminescence intensities at the end of each step were then determined (n=3).

FIG. 12 is the full-length amino acid sequence of the CBLuc for the probe constructed in Example 2. The arrows indicate the digestion sites. FIG. 12(a) shows the sequence of SEQ ID NO: 27.

FIG. 22 is determination of the androgenic activities of various ligands based on the pSimbe probe-carrying cells, in Example 2.

SEQUENCE LISTING

Figure 1:
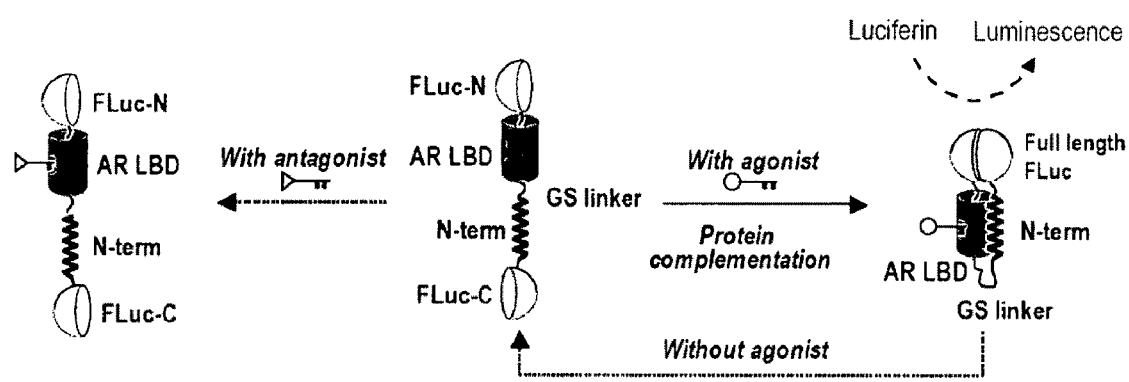
FIG. 1 is the basic strategy of the present invention for determining an AR-specific ligand.
Figure 2:
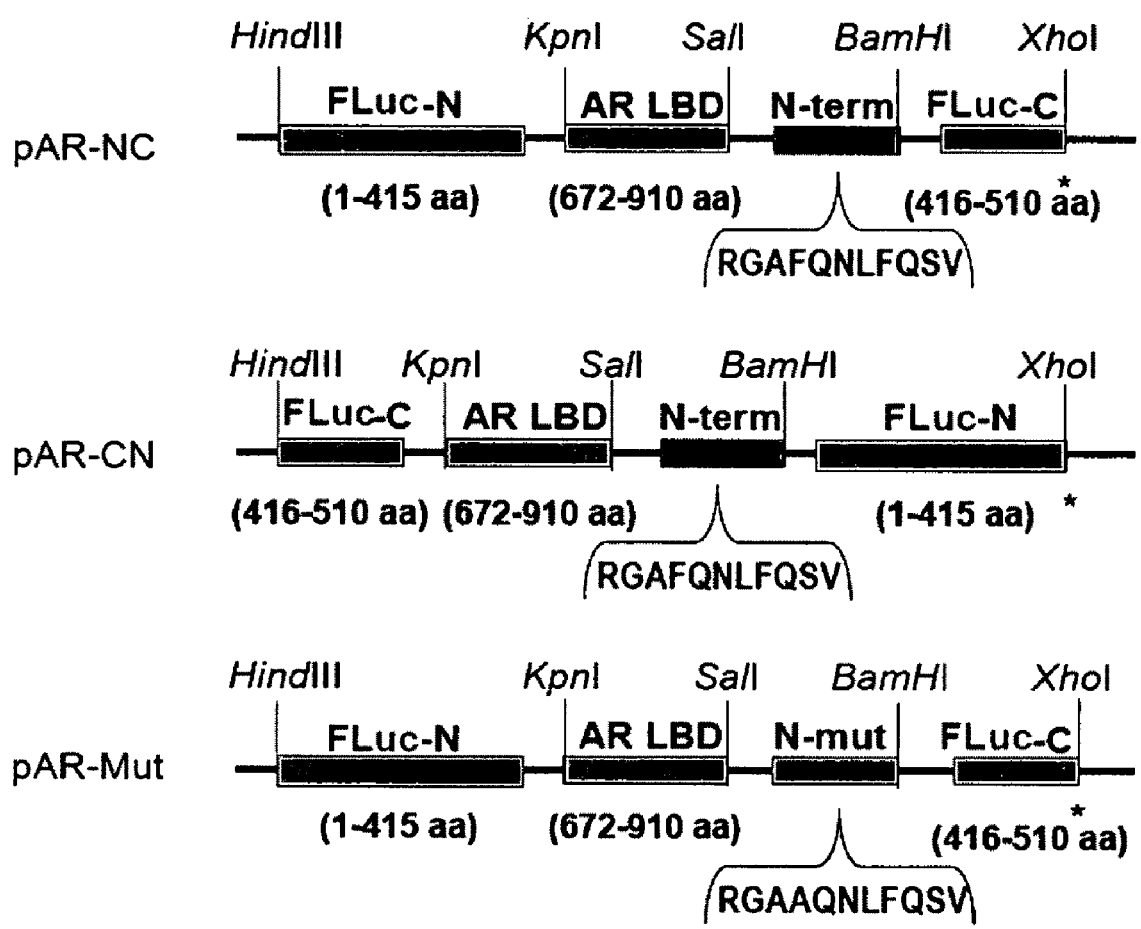
FIG. 2 is schematic structures of the probes constructed in Example 1. RGAFQNLFQSV is the sequence of SEQ ID NO: 1 and RGAAQNLFQSV is the sequence of SEQ ID NO: 30.
Figure 3:
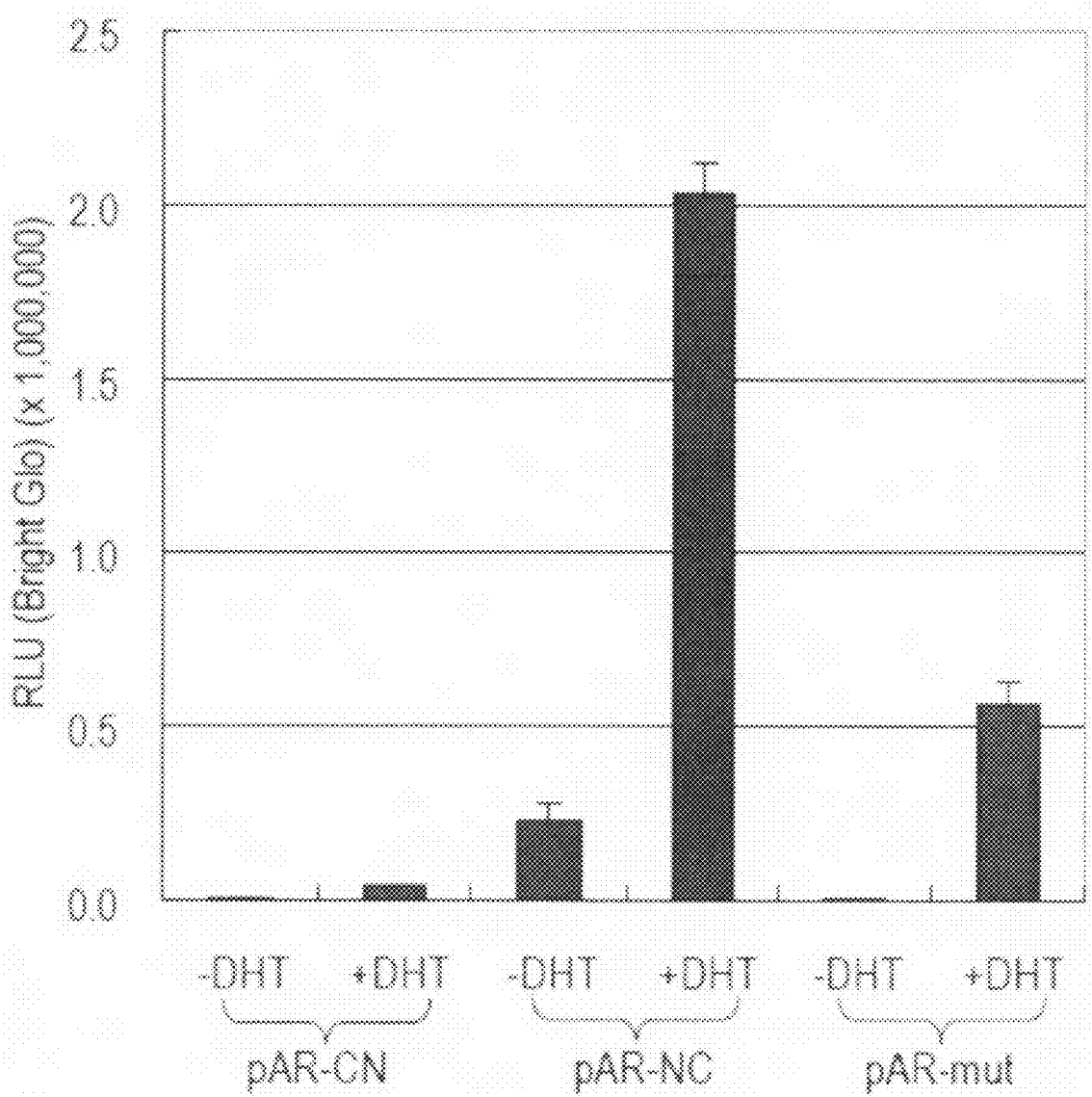
FIG. 3 is determination of the relative sensorial performance of the constructed indicators in response to $10^{-5}$ M DHT in Example 1. The DHT-induced bioluminescence intensities from the cells carrying pAR-CN, pAR-NC, or pAR-mut were compared. F24A mutation in the 'FQNLF' motif (SEQ ID NO: 28) weakened the ligand-induced AR LBD-'FQNLF' motif (SEQ ID NO: 28) association (pAR-mut) (n=3).
Figure 4:
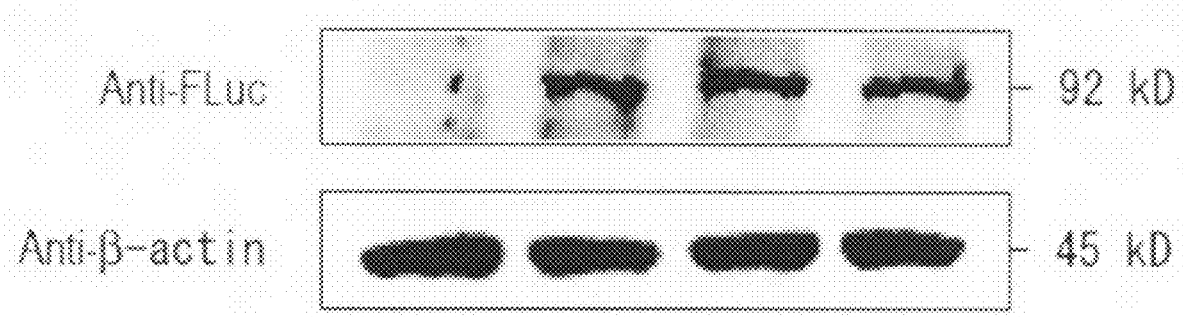
FIG. 4 is a Western blot analysis for determining the expression of the probes in Example 1. The bands represent the blots of protein lysates from intact HeLa cells (lane 1) and from the cells transfected with pAR-CN (lane 2), pAR-NC (lane 3), or pAR-mut (lane 4).
Figure 5:
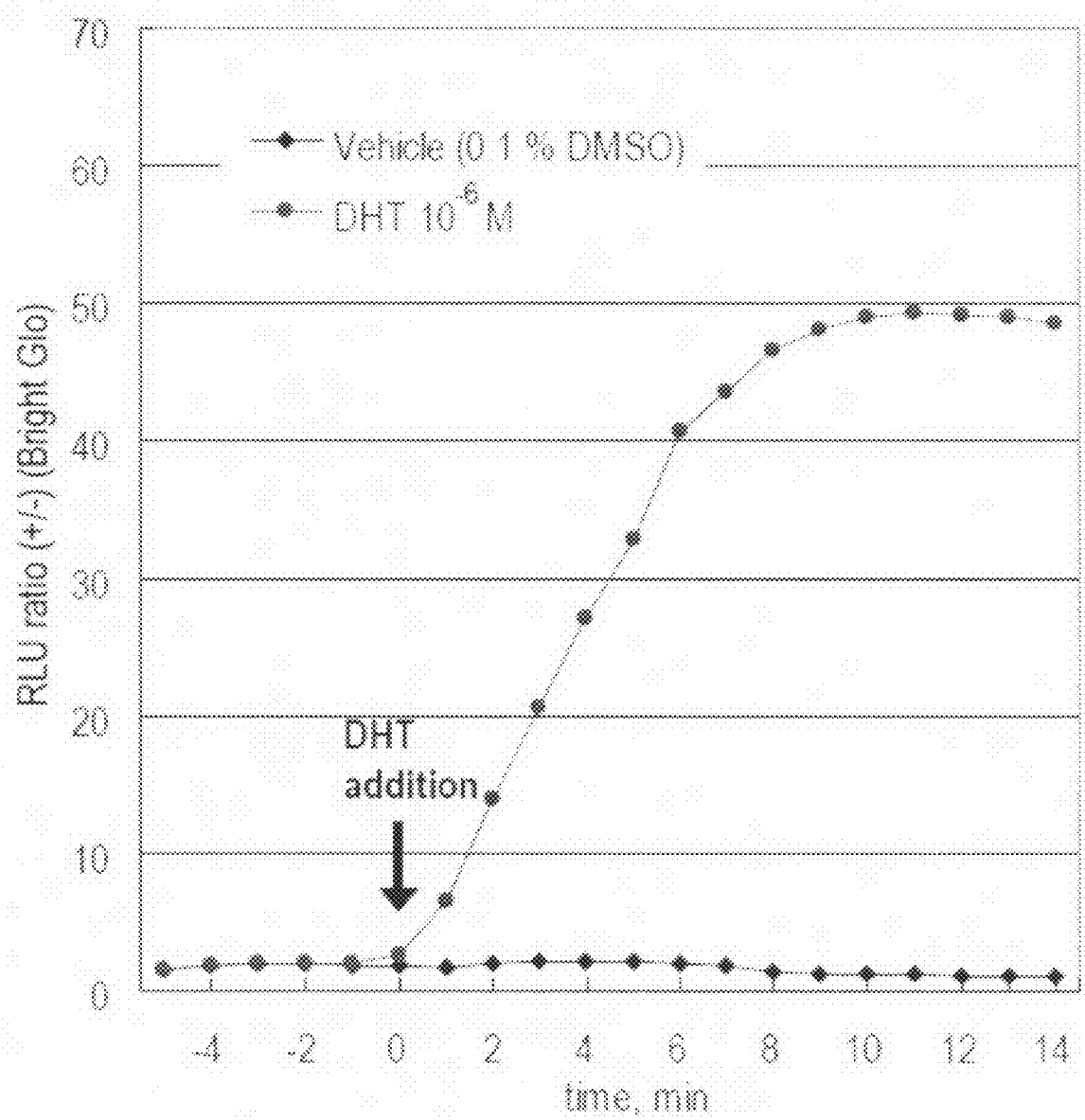
FIG. 5 is determination of the ligand-activated kinetics in the luminescence intensities from HeLa cells with pAR-NC, in Example 1. The luminescence intensities before and after the DHT addition were monitored over a one-min time interval. HeLa cells carrying pAR-NC were stimulated with $10^{-6}$ M DHT or vehicle (0.1% DMSO) at time point 0, and the dynamics of the luminescence intensities were recorded for 14 min ($t_{1/2}$=4.5 min).
Figure 6:
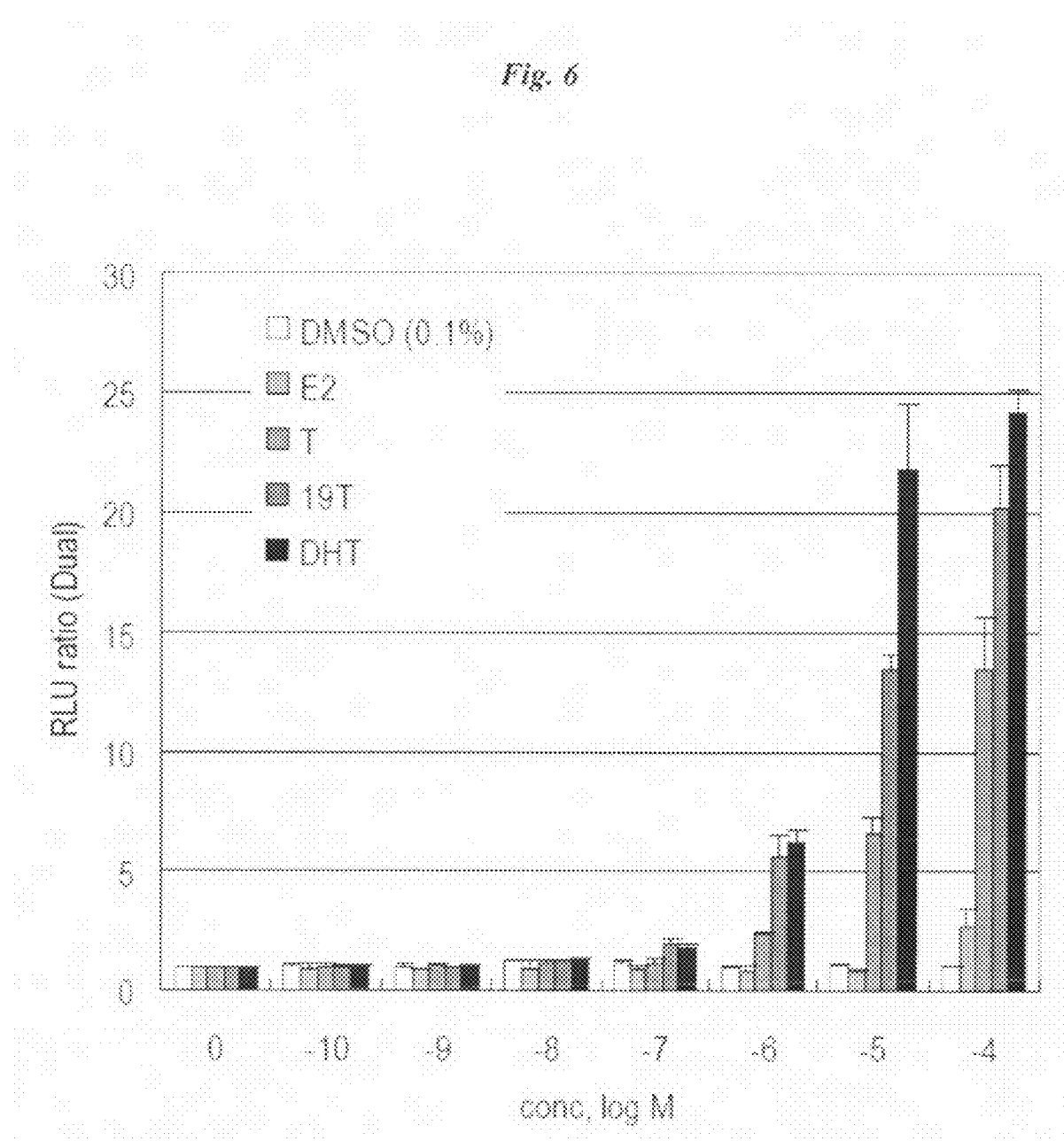
FIG. 6 is dose-response curves for steroid hormones based on the bioluminescence intensity of the complemented FLuc (n=3) measured in Example 1. Abbreviations: DHT, 5α-dihyoxytestosterone; 19T, 19-nortestosterone; T, testosterone; $E_2$, 17β-estradiol.
Figure 7:
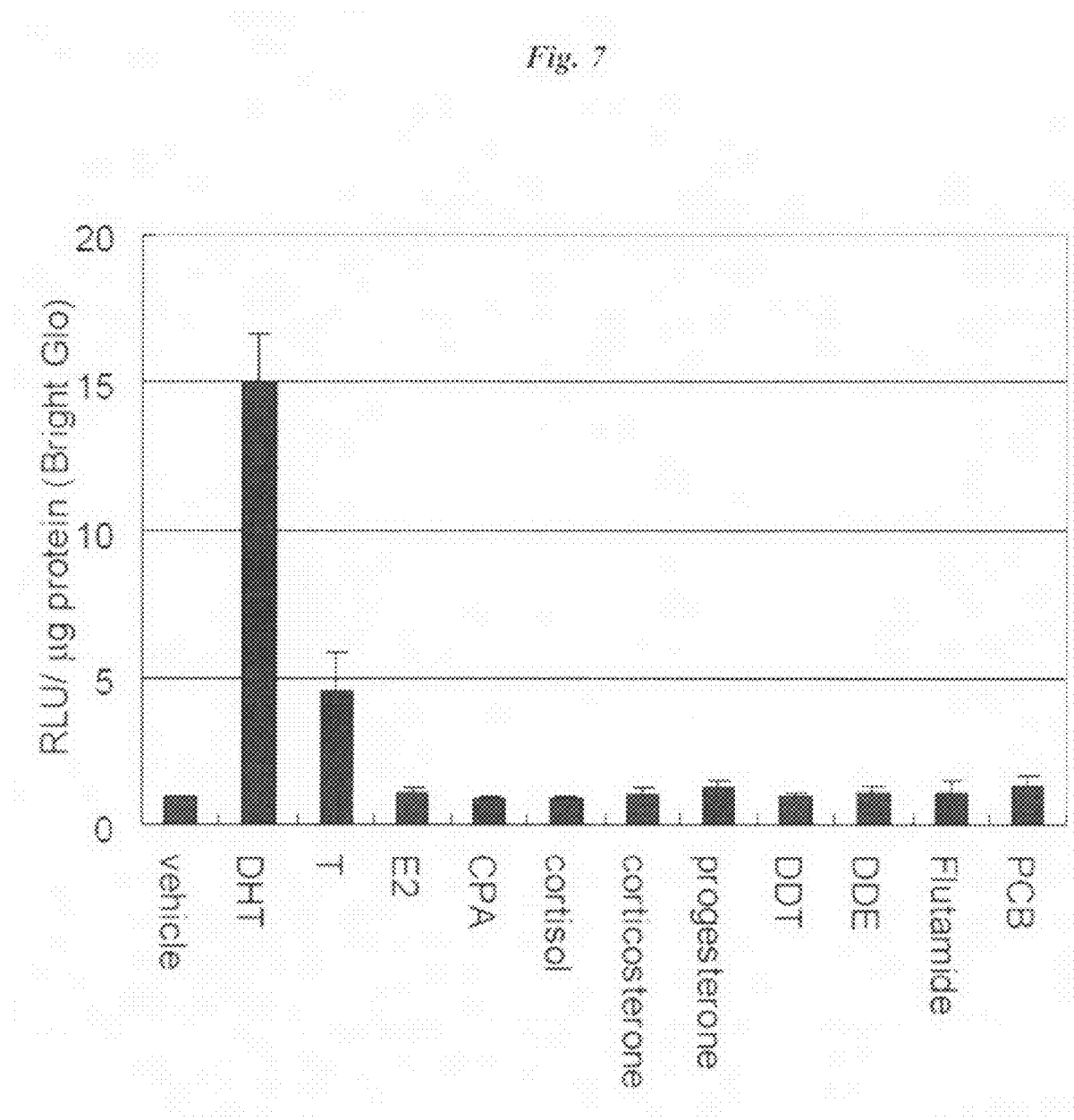
FIG. 7 is determination of the androgenic activities of ligands at $10^{-5}$ M. In Example 1, the HeLa cells carrying pAR-NC were stimulated with $10^{-5}$ M of each ligand for 20 min, and the resulting luminescence intensities were determined. Abbreviations: vehicle, 0.1% DMSO; DHT, 5α-dihyoxytestosterone; T, testosterone; $E_2$, 17β-estradiol; CPA, cyproterone acetate; DDT, 1,1,1-trichloro-2-(p-chlorophenyl)-2-(o-chlorophenyl) ethane; DDE, p,p'-dichlorodiphenyldichloroethylene; PCB, polychlorinated biphenyls (Aroclor 1254) (n=3).
Figure 8:
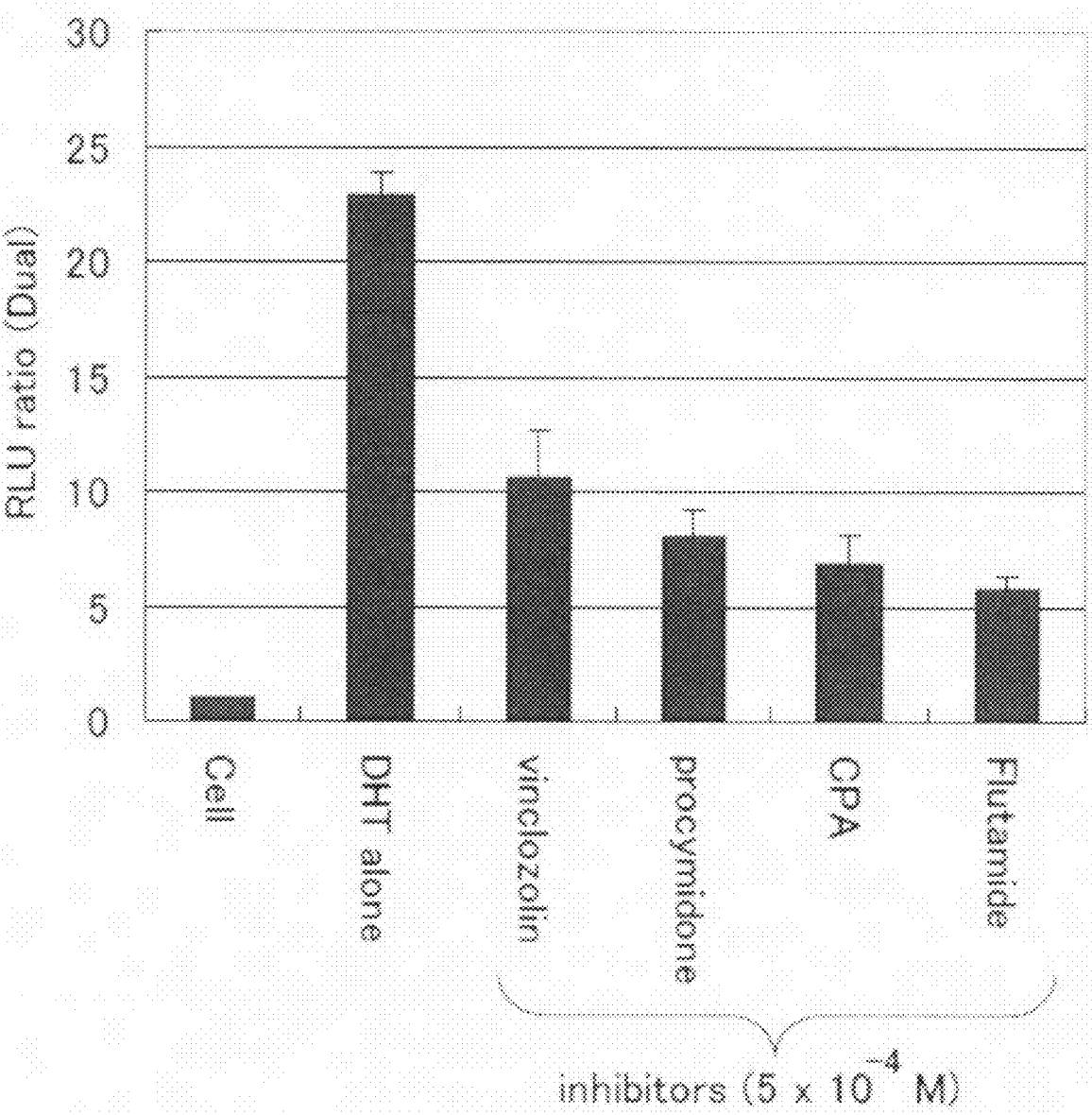
FIG. 8 is an inhibitory effect of various chemicals on the bioluminescence intensities developed by $10^{-5}$ M DHT measured in Example 1. The $5 \times 10^{-4}$ M chemicals antagonized the association of AR LBD with 'FQNLF' motif (SEQ ID NO: 28) induced by $10^{-5}$ M DHT (n=3).
Figure 9:
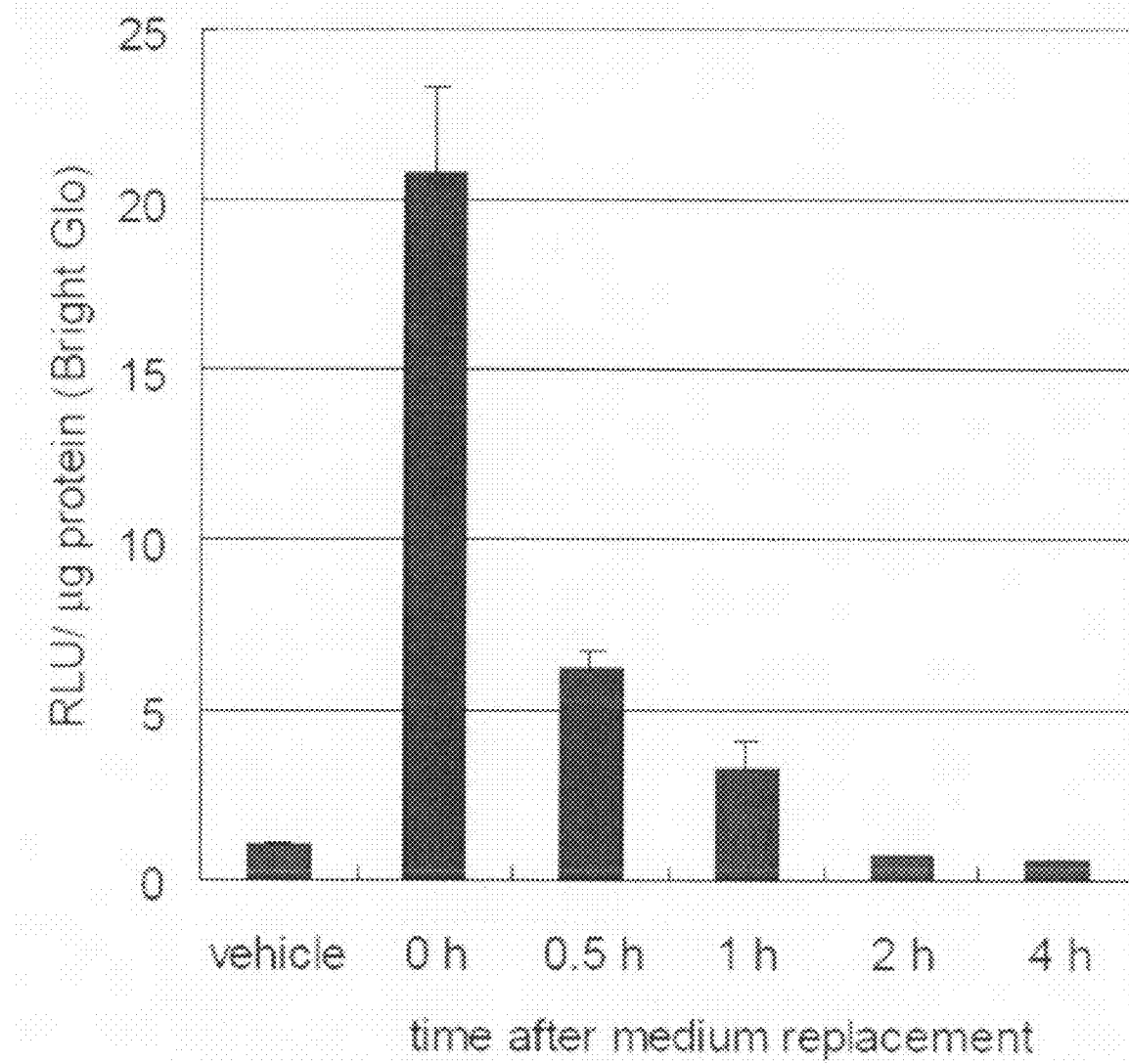
FIG. 9 is bioluminescence-based time course of the DHT-deprivation after the DHT-induced NTD-AR LBD association in Example 1.
Figure 11:
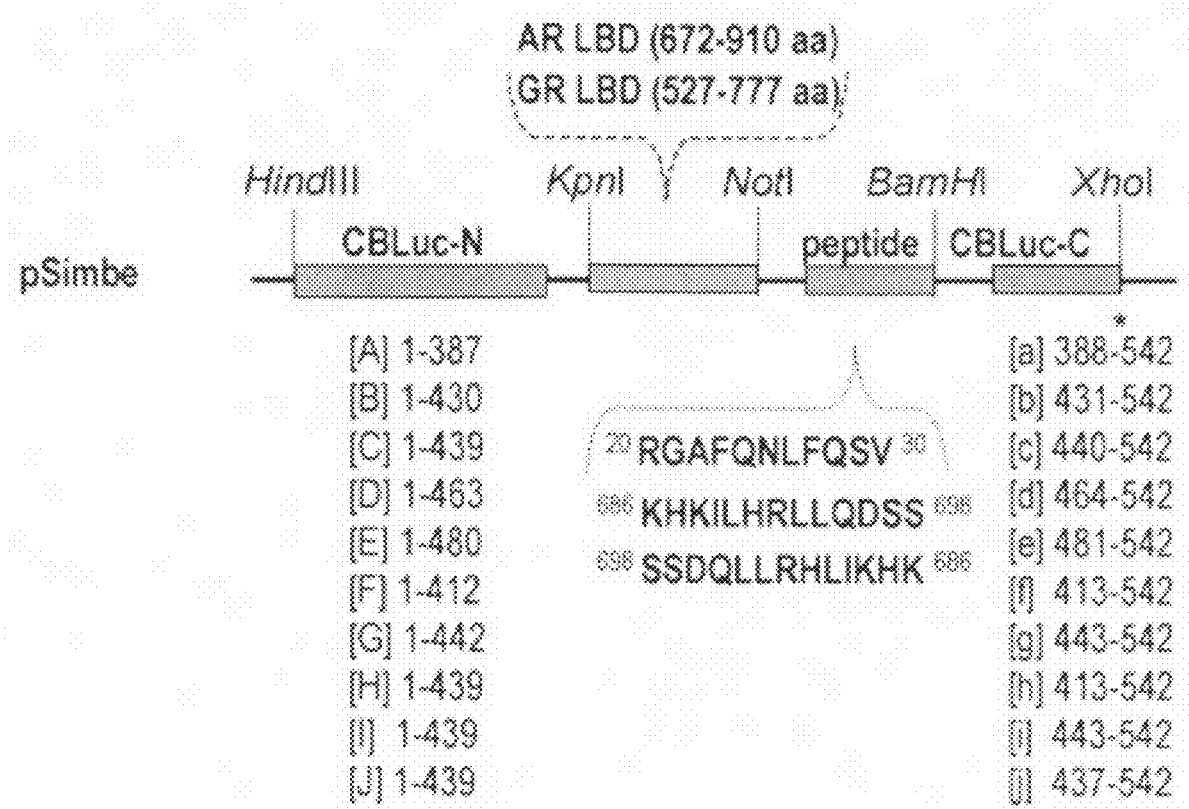
FIG. 11 is schematic structures of the probes constructed in Example 2. RGAFQNLFQSV is the sequence of SEQ ID NO: 1; KHKILHRLLQDSS is the sequence of SEQ ID NO: 2, and SSDQLLRHLIKHK is the sequence of SEQ ID NO: 3.
Figure 13:
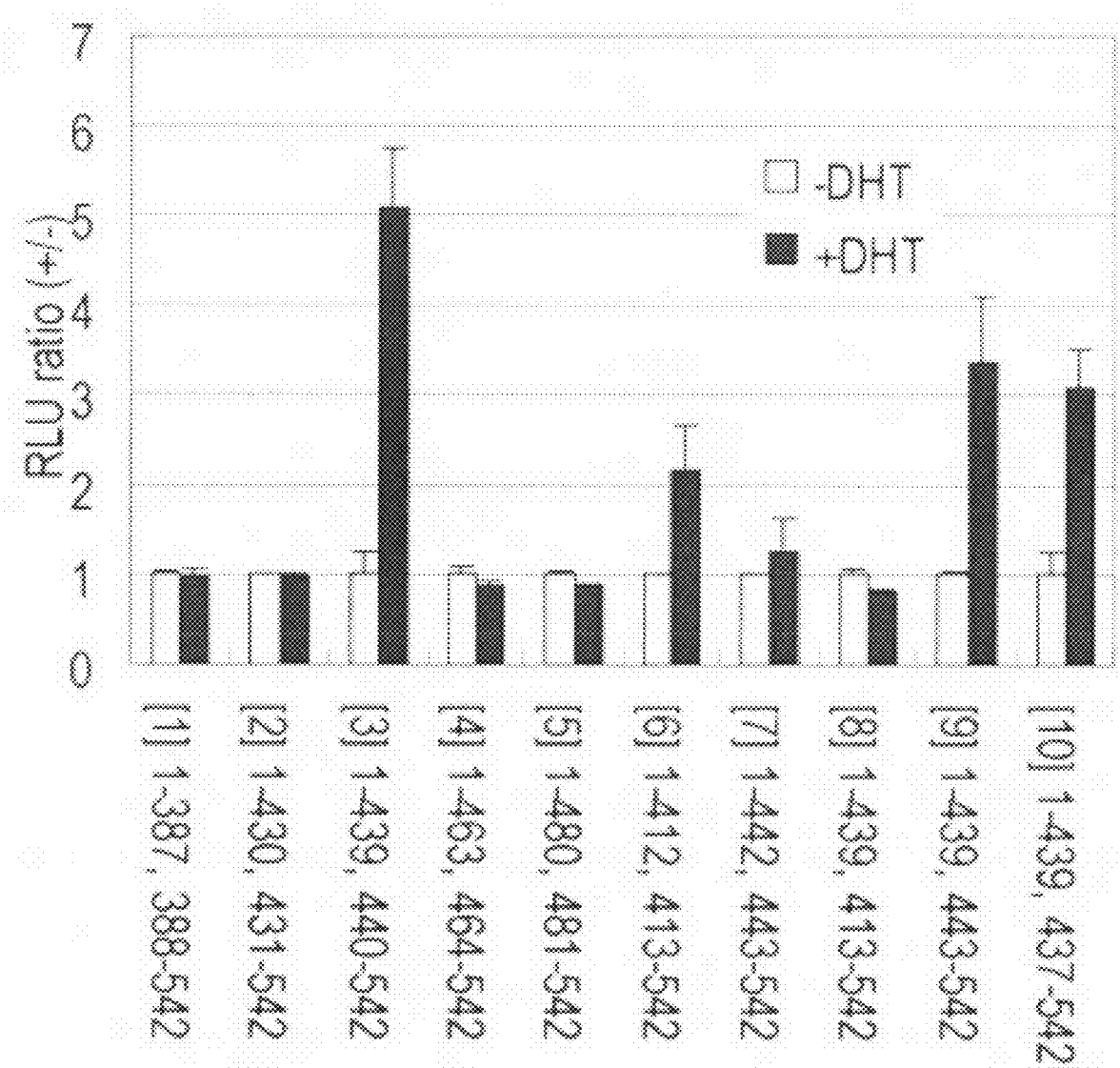
FIG. 13 is the results of the investigation of appropriate digestion sites of the CBLuc in Example 2, in which the luminescence intensity recovered by stimulation with $10^{-5}$M DHT was used as an index. The error bars are standard errors each based on three samples.
Figure 14:
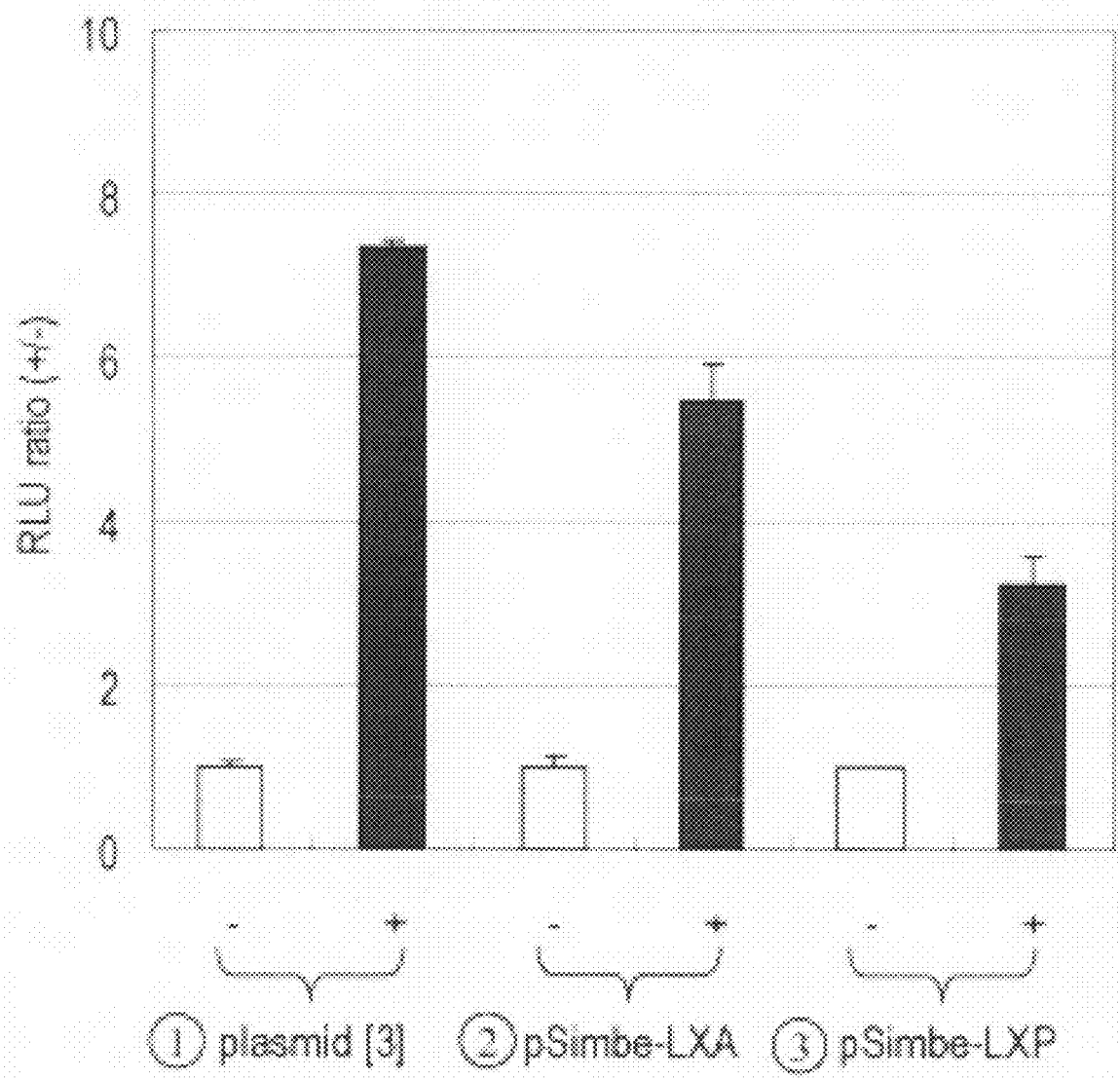
FIG. 14 is determination of the binding ability of AR LBD with various interacting peptides in Example 2.
Figure 15:
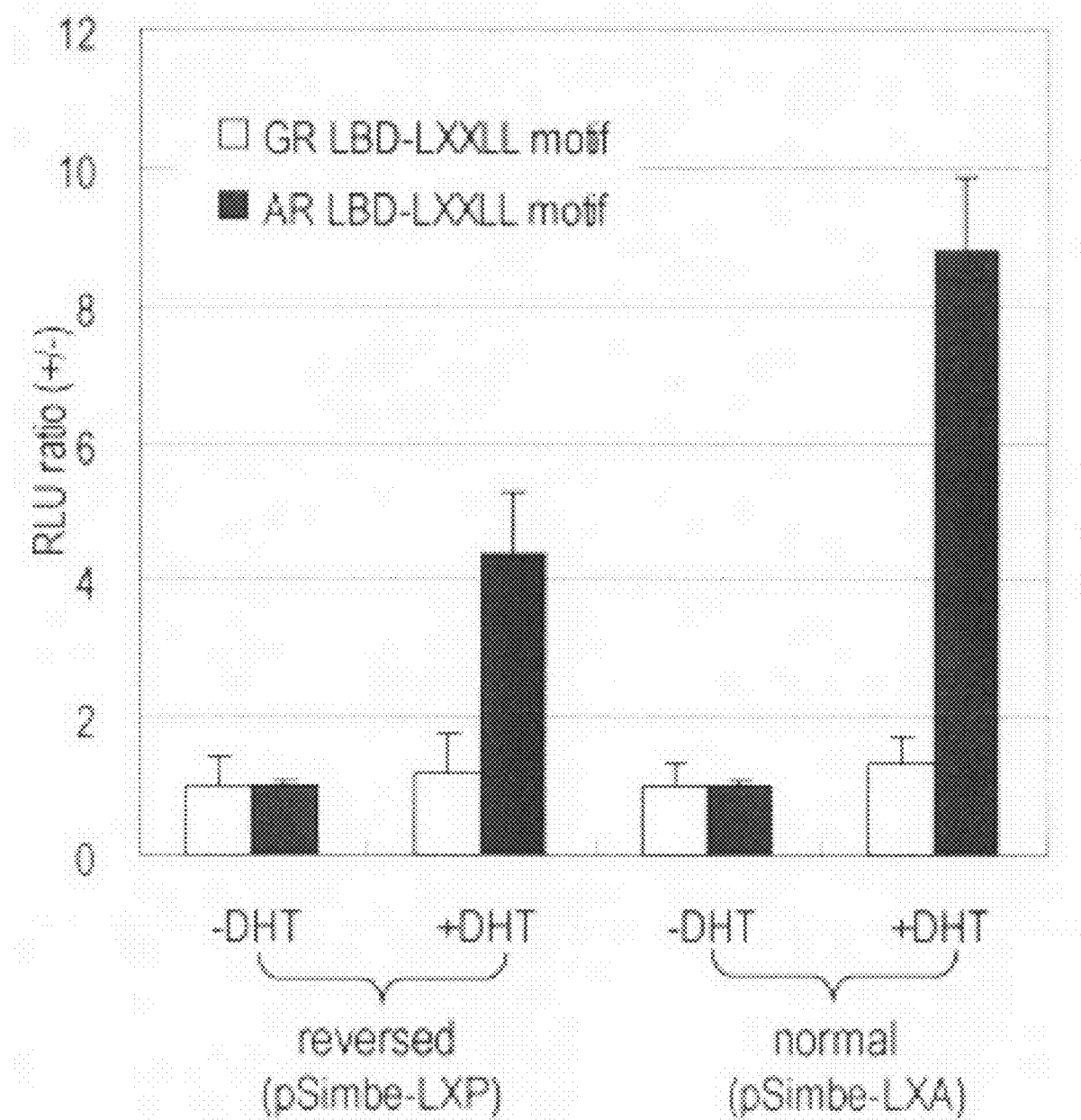
FIG. 15 the relative comparison of the luminescence intensity recovered by binding of AR LBD or GR LBD with the forward and reverse sequence of 'LXXLL' motifs, respectively, in Example 2.
Figure 16:
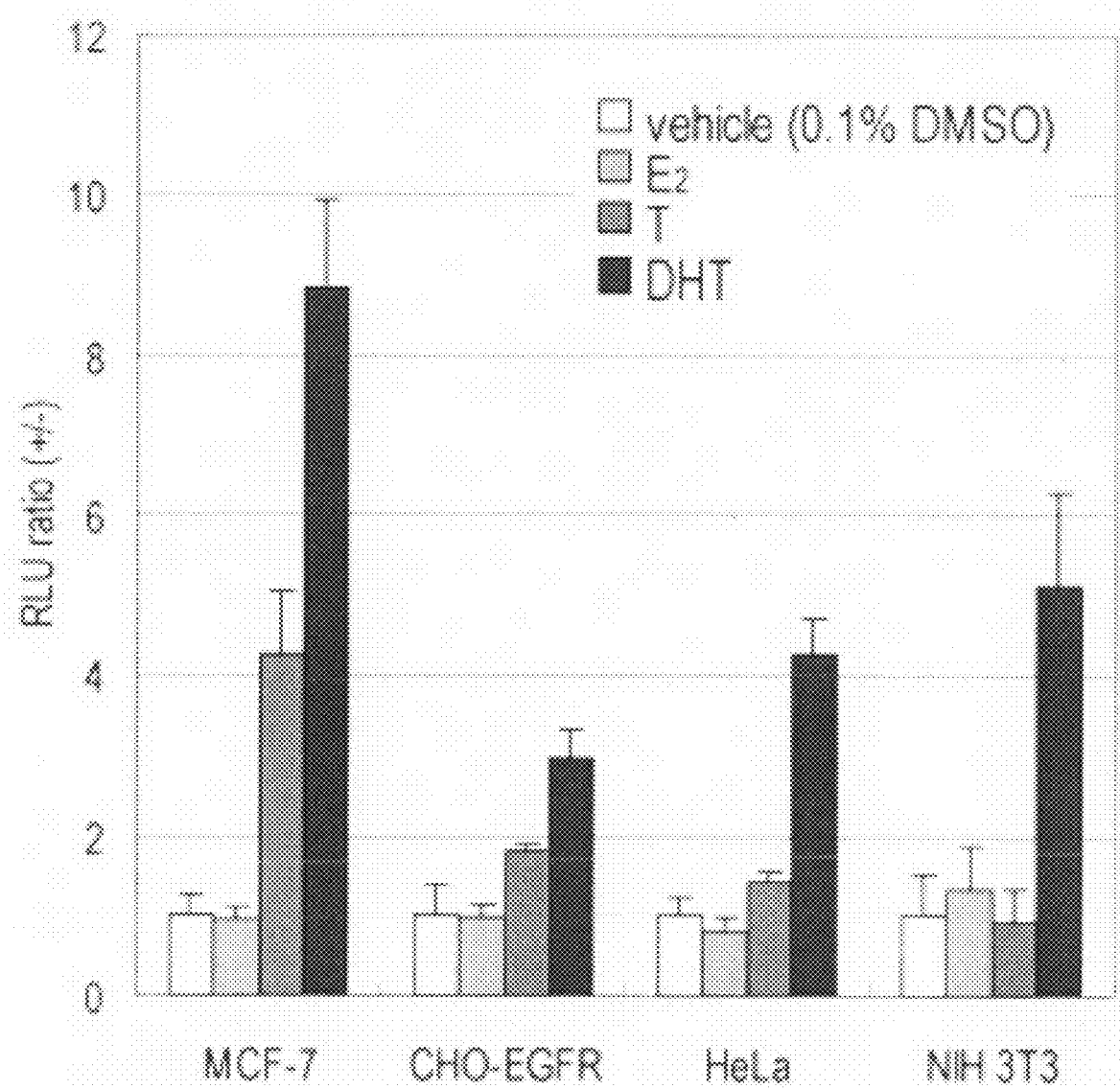
FIG. 16 is determination of relative ligand selection and sensitivity in the cell lines in Example 2.
Figure 17:
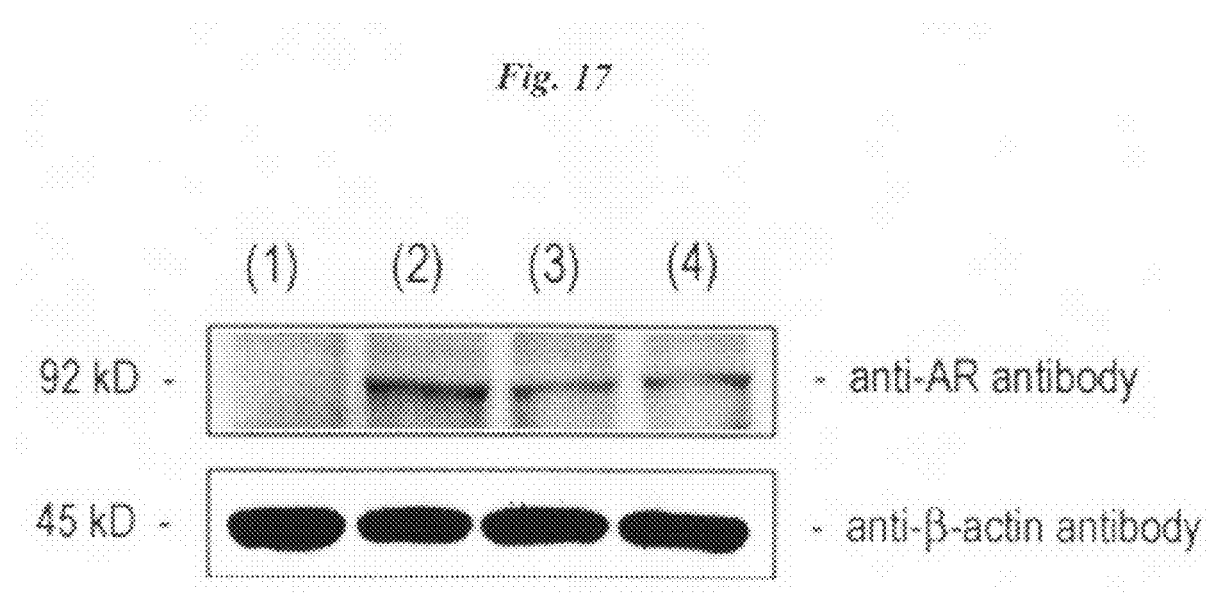
FIG. 17 is determination of the relative probe expression level from living cells carrying plasmids in Example 2 (western blotting).
Figure 18:
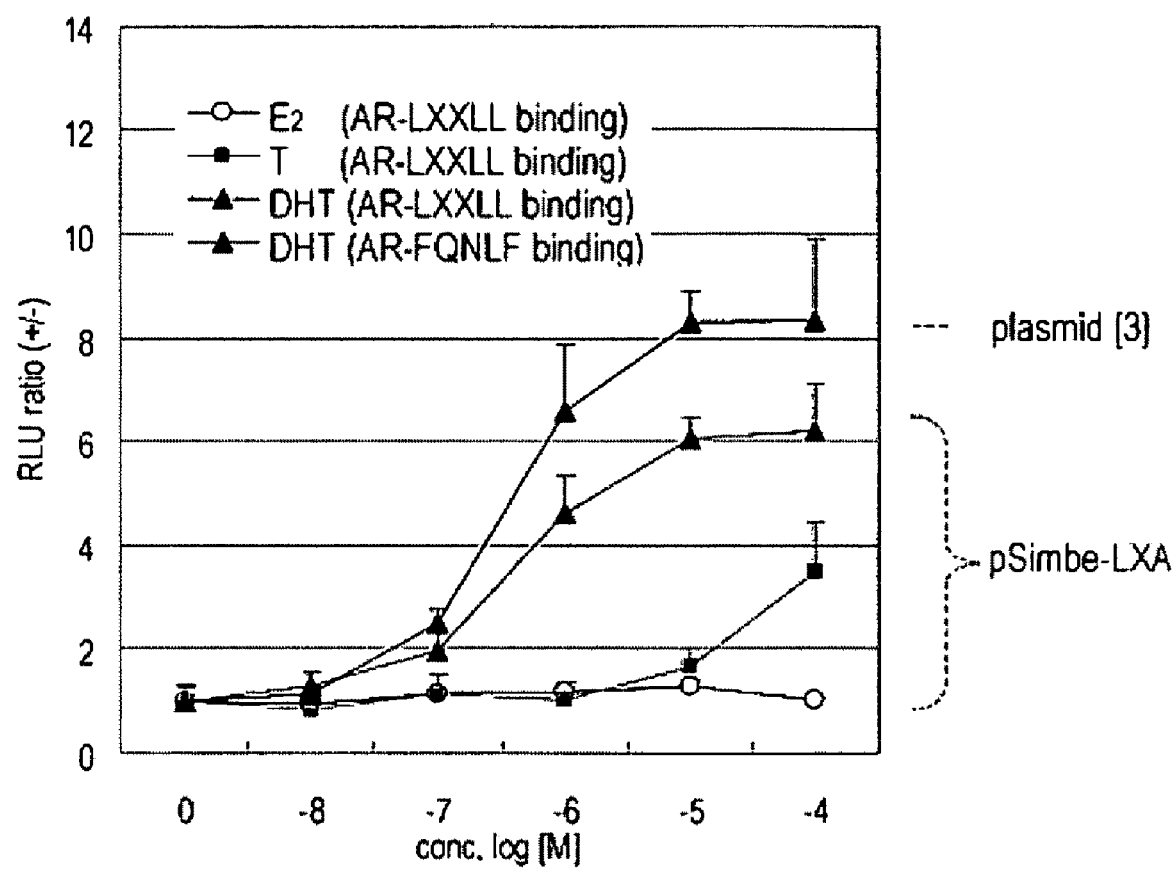
FIG. 18 is dose-response curves of various steroidal hormones on luminescence intensity after steroid-stimulation of the cells carrying pSimbi probes in Example 2. FQNLF is the sequence of SEQ ID NO: 28.
Figure 19:
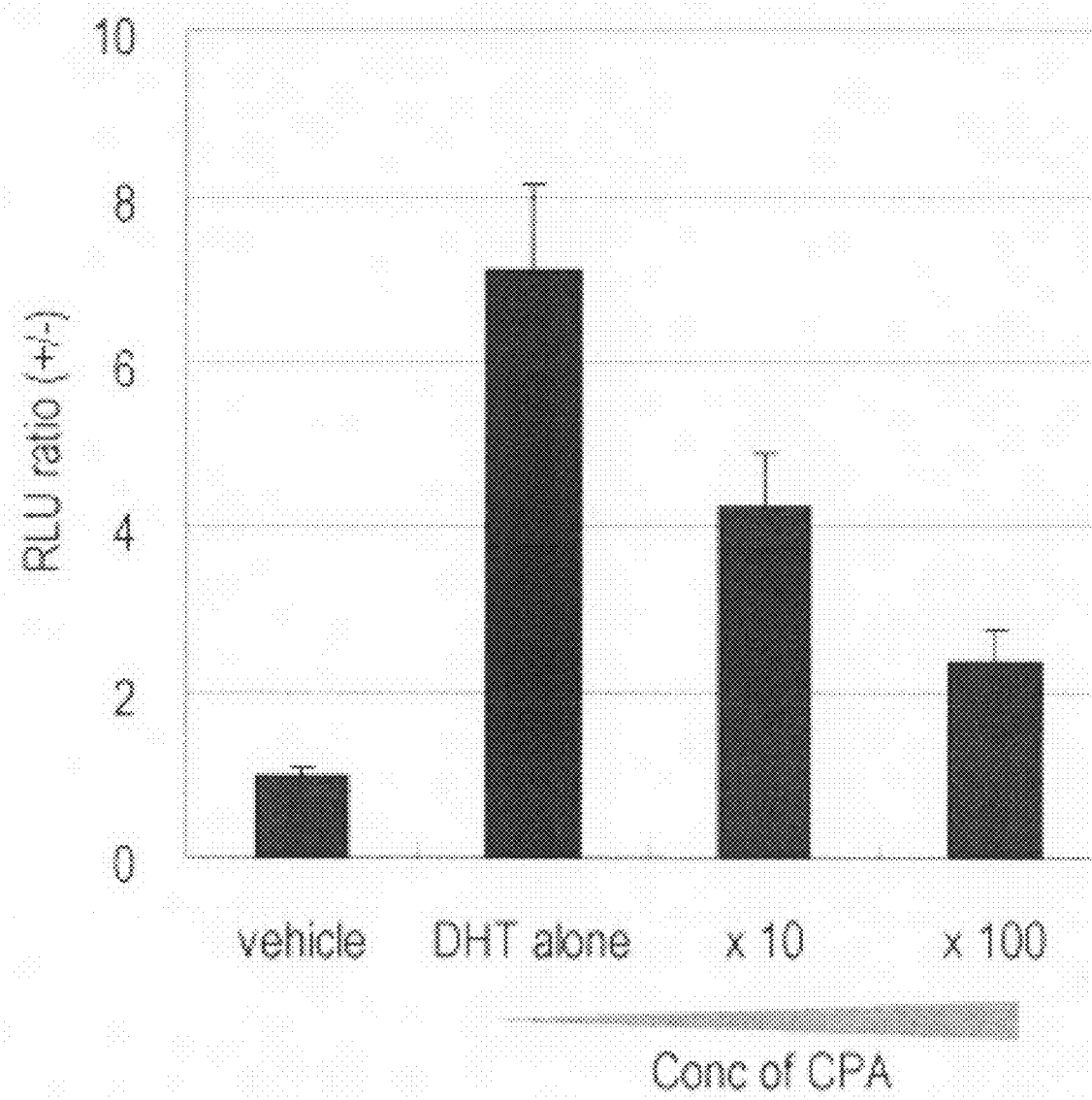
FIG. 19 is determination of the luminescence intensity from the pSimbe probe after the DHT stimulation, and subsequent inhibitory effects of antagonists in Example 2.
Figure 20:
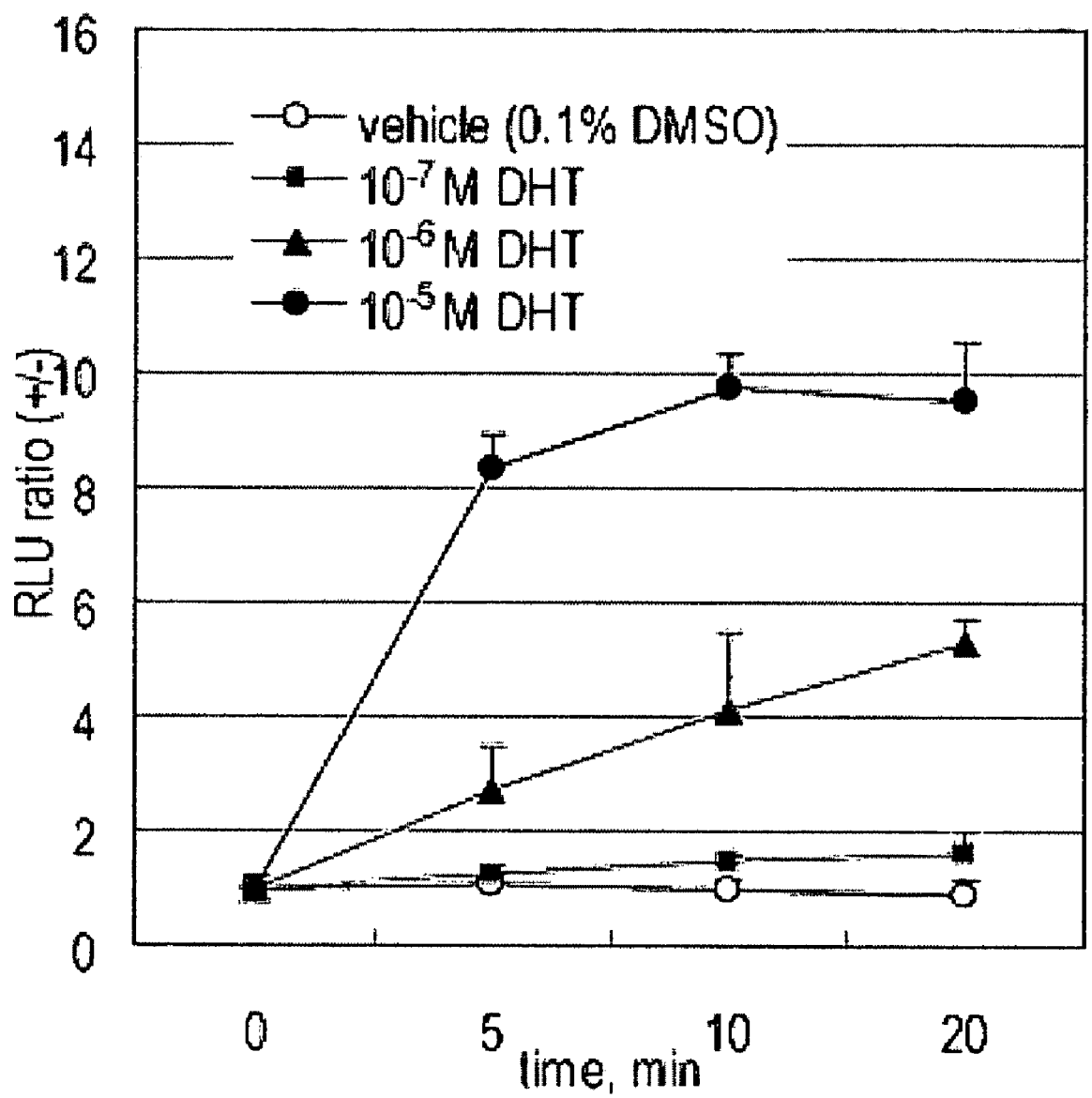
FIG. 20 is a time-course of the luminescence intensity from the pSimbe probe after the DHT stimulation in Example 2.
Figure 21:
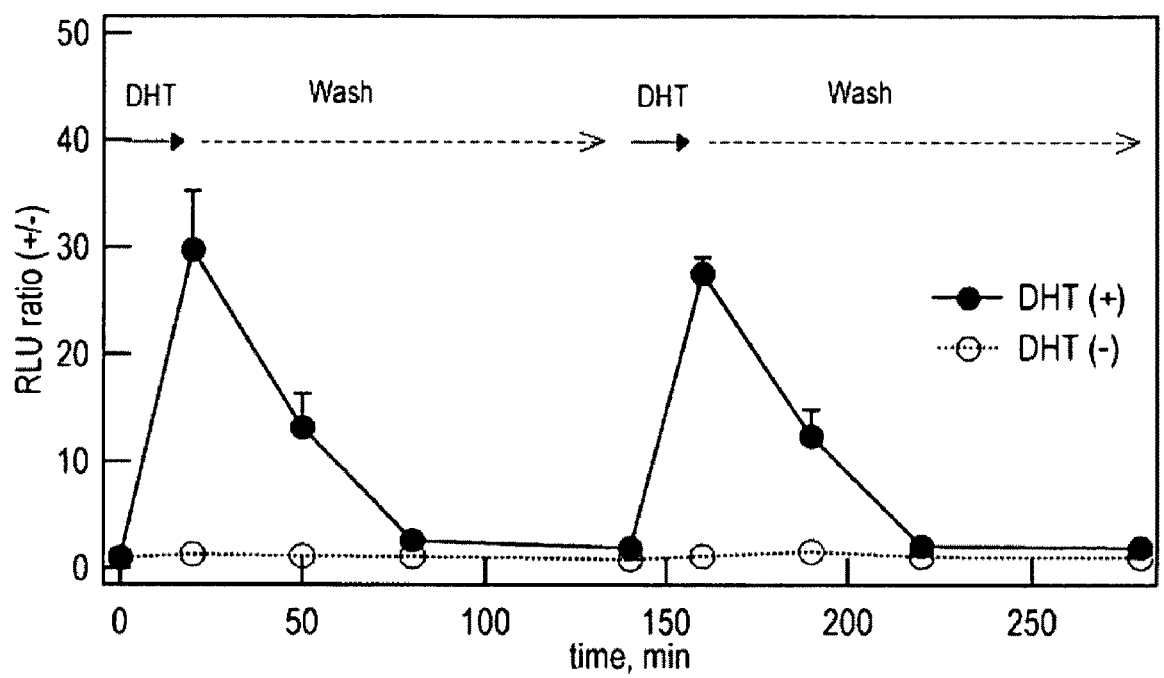
FIG. 21 is determination of the reversible ligand recognition of the pSimbe probe, and a time-course of the luminescence intensity after removal of the ligand in Example 2.

```
<160> NUMBER OF SEQ ID NOS: 31

<210> SEQ ID NO 1
<211> LENGTH: 11
<212> TYPE: PRT
<213> ORGANISM: Artificial sequence
<220> FEATURE:
<223> OTHER INFORMATION: Description of artificial sequence: Synthetic
      oligopeptide

<400> SEQUENCE: 1

Arg Gly Ala Phe Gln Asn Leu Phe Gln Ser Val
1               5                   10

<210> SEQ ID NO 2
<211> LENGTH: 13
<212> TYPE: PRT
<213> ORGANISM: Artificial sequence
<220> FEATURE:
<223> OTHER INFORMATION: Description of artificial sequence: Synthetic
      oligopeptide

<400> SEQUENCE: 2

Lys His Lys Ile Leu His Arg Leu Leu Gln Asp Ser Ser
1               5                   10

<210> SEQ ID NO 3
```

<211> LENGTH: 13
<212> TYPE: PRT
<213> ORGANISM: Artificial sequence
<220> FEATURE:
<223> OTHER INFORMATION: Description of artificial sequence: Synthetic oligopeptide

<400> SEQUENCE: 3

Ser Ser Asp Gln Leu Leu Arg His Leu Ile Lys His Lys
1               5                   10

<210> SEQ ID NO 4
<211> LENGTH: 42
<212> TYPE: DNA
<213> ORGANISM: Artificial sequence
<220> FEATURE:
<223> OTHER INFORMATION: Description of artificial sequence: Synthetic oligonucleotide

<400> SEQUENCE: 4
tttaagctta ccgccatggt aaagcgtgag aaaaatgtca tc                          42

<210> SEQ ID NO 5
<211> LENGTH: 42
<212> TYPE: DNA
<213> ORGANISM: Artificial sequence
<220> FEATURE:
<223> OTHER INFORMATION: Description of artificial sequence: Synthetic oligonucleotide

<400> SEQUENCE: 5
aaaggtaccg cctcctccca gctcgcccac ttggttcggg cc                          42

<210> SEQ ID NO 6
<211> LENGTH: 42
<212> TYPE: DNA
<213> ORGANISM: Artificial sequence
<220> FEATURE:
<223> OTHER INFORMATION: Description of artificial sequence: Synthetic oligonucleotide

<400> SEQUENCE: 6
aaaggtaccg cctcctccgt aaaaatgctc atcttcgtcg ta                          42

<210> SEQ ID NO 7
<211> LENGTH: 42
<212> TYPE: DNA
<213> ORGANISM: Artificial sequence
<220> FEATURE:
<223> OTHER INFORMATION: Description of artificial sequence: Synthetic oligonucleotide

<400> SEQUENCE: 7
aaaggtaccg cctcctccga tcagctcctt gtaacgatcc ac                          42

<210> SEQ ID NO 8
<211> LENGTH: 42
<212> TYPE: DNA
<213> ORGANISM: Artificial sequence
<220> FEATURE:
<223> OTHER INFORMATION: Description of artificial sequence: Synthetic oligonucleotide

<400> SEQUENCE: 8
aaaggtaccg cctcctccat cgcgaatgca tggatttttc aa                          42

<210> SEQ ID NO 9
<211> LENGTH: 42

```
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 9
aaaggtaccg cctcctccag cagaaggcag ttcgccggcc tc                              42

<210> SEQ ID NO 10
<211> LENGTH: 42
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 10
aaaggtaccg cctcctccgt cgtcgtcgat ggcctccttg gt                              42

<210> SEQ ID NO 11
<211> LENGTH: 42
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 11
aaaggtaccg cctcctccct tgtatttgat cagctccttg ta                              42

<210> SEQ ID NO 12
<211> LENGTH: 42
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 12
tttggatccg gaggcggctg tatcaaaggc cctatggtga gc                              42

<210> SEQ ID NO 13
<211> LENGTH: 42
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 13
tttggatccg gaggcggcgt cgtggatcgt tacaaggagc tg                              42

<210> SEQ ID NO 14
<211> LENGTH: 42
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 14
tttggatccg gaggcggcaa atacaagggt agccaggttg ct                              42

<210> SEQ ID NO 15
<211> LENGTH: 42
<212> TYPE: DNA
<213> ORGANISM: Artificial sequence
```

```
<220> FEATURE:
<223> OTHER INFORMATION: Description of artificial sequence: Synthetic
      oligonucleotide

<400> SEQUENCE: 15
tttggatccg gaggcggcgt cgctgtggtc ggcattcctg at                          42

<210> SEQ ID NO 16
<211> LENGTH: 42
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 16
tttggatccg gaggcggctt cgttgtcaag cagcctggta ca                          42

<210> SEQ ID NO 17
<211> LENGTH: 42
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 17
tttggatccg gaggcggcgg ctggttgcat tctggtgatt tt                          42

<210> SEQ ID NO 18
<211> LENGTH: 42
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 18
tttggatccg gaggcggcgg tagccaggtt gctccagctg ag                          42

<210> SEQ ID NO 19
<211> LENGTH: 42
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 19
tttggatccg gaggcggcga gctgatcaaa tacaaggta gc                           42

<210> SEQ ID NO 20
<211> LENGTH: 36
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 20
aaatttctcg agctaaccgc cggccttcac caacaa                                 36

<210> SEQ ID NO 21
<211> LENGTH: 72
<212> TYPE: DNA
<213> ORGANISM: Artificial sequence
<220> FEATURE:
<223> OTHER INFORMATION: Description of artificial sequence: Synthetic
```

-continued oligonucleotide

<400> SEQUENCE: 21
tatgaattcg tcgacggcgg caacggcggc cgaggagctt tccagaatct gttccagagc    60
gtgggatcct ta                                                        72

<210> SEQ ID NO 22
<211> LENGTH: 72
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 22
taaggatccc acgctctgga acagattctg gaaagctcct cggccgccgt tgccgccgtc    60
gacgaattca ta                                                        72

<210> SEQ ID NO 23
<211> LENGTH: 66
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 23
aaagtcgacg gcggccgcaa gcataaaatt ttgcacagac tccttcagga cagtagtgga    60
tccttt                                                               66

<210> SEQ ID NO 24
<211> LENGTH: 66
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 24
aaaggatcca ctactgtcct gaaggagtct gtgcaaaatt ttatgcttgc ggccgccgtc    60
gacttt                                                               66

<210> SEQ ID NO 25
<211> LENGTH: 66
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 25
aaagtcgacg gcggccgcag tagtgaccag cttctcagac acttgattaa acataaggga    60
tcctttt                                                              66

<210> SEQ ID NO 26
<211> LENGTH: 66
<212> TYPE: DNA
<213> ORGANISM: Artificial sequence
<220> FEATURE:
<223> OTHER INFORMATION: Description of artificial sequence: Synthetic
      oligonucleotide

<400> SEQUENCE: 26
aaaggatccc ttatgtttaa tcaagtgtct gagaagctgg tcactactgc ggccgccgtc    60

```
gactttt                                                          66
```

<210> SEQ ID NO 27
<211> LENGTH: 542
<212> TYPE: PRT
<213> ORGANISM: Pyrophorus plagiophthalamus
<300> PUBLICATION INFORMATION:
<308> DATABASE ACCESSION NUMBER: GenBank/AY258592.1
<309> DATABASE ENTRY DATE: 2003-07-18
<313> RELEVANT RESIDUES IN SEQ ID NO: (1)..(542)

<400> SEQUENCE: 27

```
Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
    210                 215                 220

Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Thr Leu Gly Asp
            340                 345                 350
```

```
Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
        370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
                420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
        450                 455                 460

Ala Val Val Gly Ile Pro Asp Leu Glu Ala Gly Glu Leu Pro Ser Ala
465                 470                 475                 480

Phe Val Val Lys Gln Pro Gly Thr Glu Ile Thr Ala Lys Glu Val Tyr
                485                 490                 495

Asp Tyr Leu Ala Glu Arg Val Ser His Thr Lys Tyr Leu Arg Gly Gly
        500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Val Lys Ala Gly Gly
        530                 535                 540

<210> SEQ ID NO 28
<211> LENGTH: 5
<212> TYPE: PRT
<213> ORGANISM: Artificial Sequence
<220> FEATURE:
<223> OTHER INFORMATION: Description of artificial sequence: Synthetic
      oligopeptide

<400> SEQUENCE: 28

Phe Gln Asn Leu Phe
1               5

<210> SEQ ID NO 29
<211> LENGTH: 5
<212> TYPE: PRT
<213> ORGANISM: Artificial Sequence
<220> FEATURE:
<223> OTHER INFORMATION: Description of artificial sequence: Synthetic
      oligopeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 29

Leu Xaa Xaa Leu Leu
1               5

<210> SEQ ID NO 30
<211> LENGTH: 11
<212> TYPE: PRT
<213> ORGANISM: Artificial Sequence
<220> FEATURE:
<223> OTHER INFORMATION: Description of artificial sequence: Synthetic
      oligopeptide

<400> SEQUENCE: 30
```

```
Arg Gly Ala Ala Gln Asn Leu Phe Gln Ser Val
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Description of artificial sequence: Synthetic
      oligopeptide

<400> SEQUENCE: 31

Ala Gln Asn Leu Phe
1               5
```

The invention claimed is:

1. A single molecule-format bioluminescent probe for detecting a target-specific ligand in a living cell, which comprises,
   a ligand-binding molecule of which conformation is changed upon binding to the ligand, wherein the ligand-binding molecule comprises a ligand-binding domain (LBD) of a nuclear receptor and an LBD-interacting domain that is a coactivator peptide of said nuclear receptor, and
   an N-terminal polypeptide and a C-terminal polypeptide of a click beetle luciferase (N-CBLuc and C-CBLuc), which flank each end of the ligand-binding molecule, respectively, wherein the N-CBLuc and the C-CBLuc self-complement to generate a luminescent signal only upon binding of the ligand to the ligand-binding molecule, and
wherein
   N-CBLuc consists of the sequence of amino acids 1-412 of SEQ ID NO: 27 and
   C-CBLuc consists of the sequence of amino acids 413-542 of SEQ ID NO: 27, OR
   N-CBLuc consists of the sequence of
      amino acids 1-439 of SEQ ID NO: 27 or
      amino acids 1-442 of SEQ ID NO: 27 and
   C-CBLuc consists of the sequence of
      amino acids 437-542 of SEQ ID NO: 27 or
      amino acids 443-542 of SEQ ID NO: 27.

2. The probe of claim 1, wherein the LBD is of an androgen receptor (AR) and the coactivator peptide is a peptide comprising an AR N-terminal 'FQNLF' motif having the sequence of SEQ ID NO: 28 or a peptide comprising a Xenopus TIF2 'LXXLL' motif having the sequence of SEQ ID NO: 29.

3. An expression vector capable of expressing the probe of claim 1 in a living cell.

4. A ligand detection kit comprising
   a substrate for CBLuc
   and
   the probe of claim 1 or an expression vector capable of expressing the probe in a living cell.

5. An in vitro method for screening an unknown agonist to LBD, comprising:
   (1) introducing the probe of claim 1 into a living cell;
   (2) contacting the living cell with a candidate substance; and
   (3) detecting a luminescence signal and thereby identifying an agonist candidate substance.

6. The agonist screening method according to claim 5, wherein the probe is introduced into the living cell by introducing into the living cell an expression vector capable of expressing the probe in the living cell.

7. An in vitro method for screening an unknown antagonist which inhibits the binding of a known agonist with an LBD, comprising:
   (1) introducing the probe of claim 1 into a living cell;
   (2) contacting the living cell with a candidate substance;
   (3) contacting the living cell with the known agonist; and
   (4) detecting a luminescence signal and thereby identifying an antagonist candidate substance.

8. The antagonist screening method according to claim 7, wherein the probe is introduced into the living cell by introducing into the living cell an expression vector capable of expressing the probe in the living cell.

* * * * *